US009523614B2

(12) United States Patent
Hermsen et al.

(10) Patent No.: US 9,523,614 B2
(45) Date of Patent: Dec. 20, 2016

(54) DEVICE AND METHOD FOR DETERMINING STERILIZATION CONDITIONS

(76) Inventors: Robbert-Jan Hermsen, Steijl-Venlo (NL); Knut Schumacher, Neuss (DE)

( * ) Notice: Subject to any disclaimer, the term of this patent is extended or adjusted under 35 U.S.C. 154(b) by 0 days.

(21) Appl. No.: 13/823,563

(22) PCT Filed: Sep. 16, 2011

(86) PCT No.: PCT/US2011/051878
§ 371 (c)(1),
(2), (4) Date: Mar. 14, 2013

(87) PCT Pub. No.: WO2012/037431
PCT Pub. Date: Mar. 22, 2012

(65) Prior Publication Data
US 2013/0177042 A1   Jul. 11, 2013

(30) Foreign Application Priority Data
Sep. 17, 2010   (GB) .................... 1015526.5

(51) Int. Cl.
*G01K 7/00*  (2006.01)
*G01K 1/00*  (2006.01)
*G01K 7/02*  (2006.01)
*A61L 2/28*  (2006.01)

(52) U.S. Cl.
CPC . *G01K 7/02* (2013.01); *A61L 2/28* (2013.01); *G01K 1/00* (2013.01)

(58) Field of Classification Search
USPC ............. 374/179, 208, 141, 166, 112, 137, 143,374/45
See application file for complete search history.

(56) References Cited

U.S. PATENT DOCUMENTS

| 3,982,893 | A | | 9/1976 | Joslyn | |
|---|---|---|---|---|---|
| 4,728,369 | A | * | 3/1988 | Hammerslag et al. | 136/230 |
| 4,865,814 | A | | 9/1989 | Childress | |
| 5,121,994 | A | * | 6/1992 | Molitoris | 374/179 |
| 2002/0034823 | A1 | * | 3/2002 | Kuepper et al. | 436/1 |
| 2003/0063997 | A1 | | 4/2003 | Fryer | |

FOREIGN PATENT DOCUMENTS

| EP | 0 419 282 | 7/1993 |
|---|---|---|
| EP | 0 854 733 | 7/1998 |
| EP | 1 230 936 | 8/2002 |
| JP | 11-513285 | 11/1999 |
| WO | 97/12637 | 4/1997 |
| WO | 9729789 | 8/1997 |

OTHER PUBLICATIONS

ASTM Standard B258, 2008.*
International Search Report PCT/US2011/051878; Dec. 1, 2011; 3 pgs.

* cited by examiner

*Primary Examiner* — Mirellys Jagan

(57) ABSTRACT

Devices for determining sterilization conditions within a sterilization chamber are described. Such devices include an elongate tube to be placed within said sterilization chamber and at least two temperature sensors within the cavity of the elongate tube. The at least two temperature sensors are spaced apart from each other along the length of the elongate tube by a predetermined distance and spaced apart from the interior wall of the elongate tube. Methods for determining sterilization discussed.

12 Claims, 15 Drawing Sheets

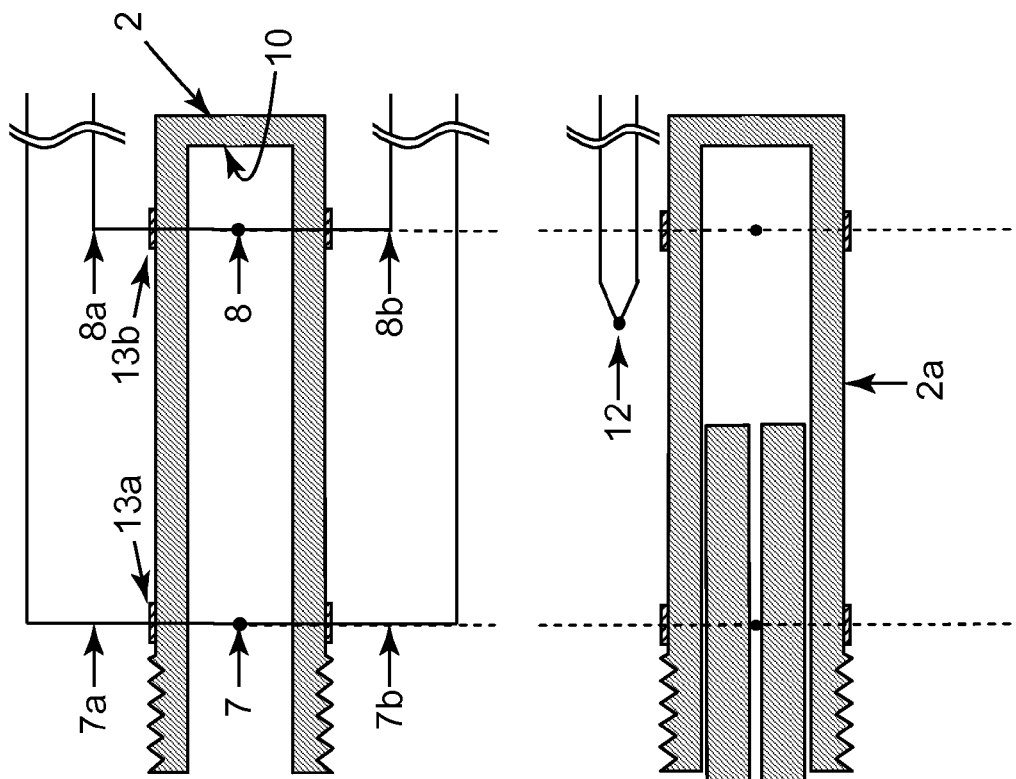
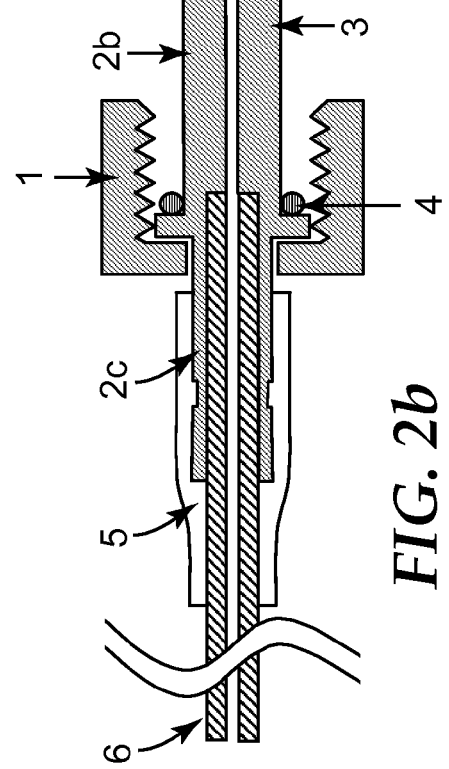
FIG. 2a
FIG. 2b

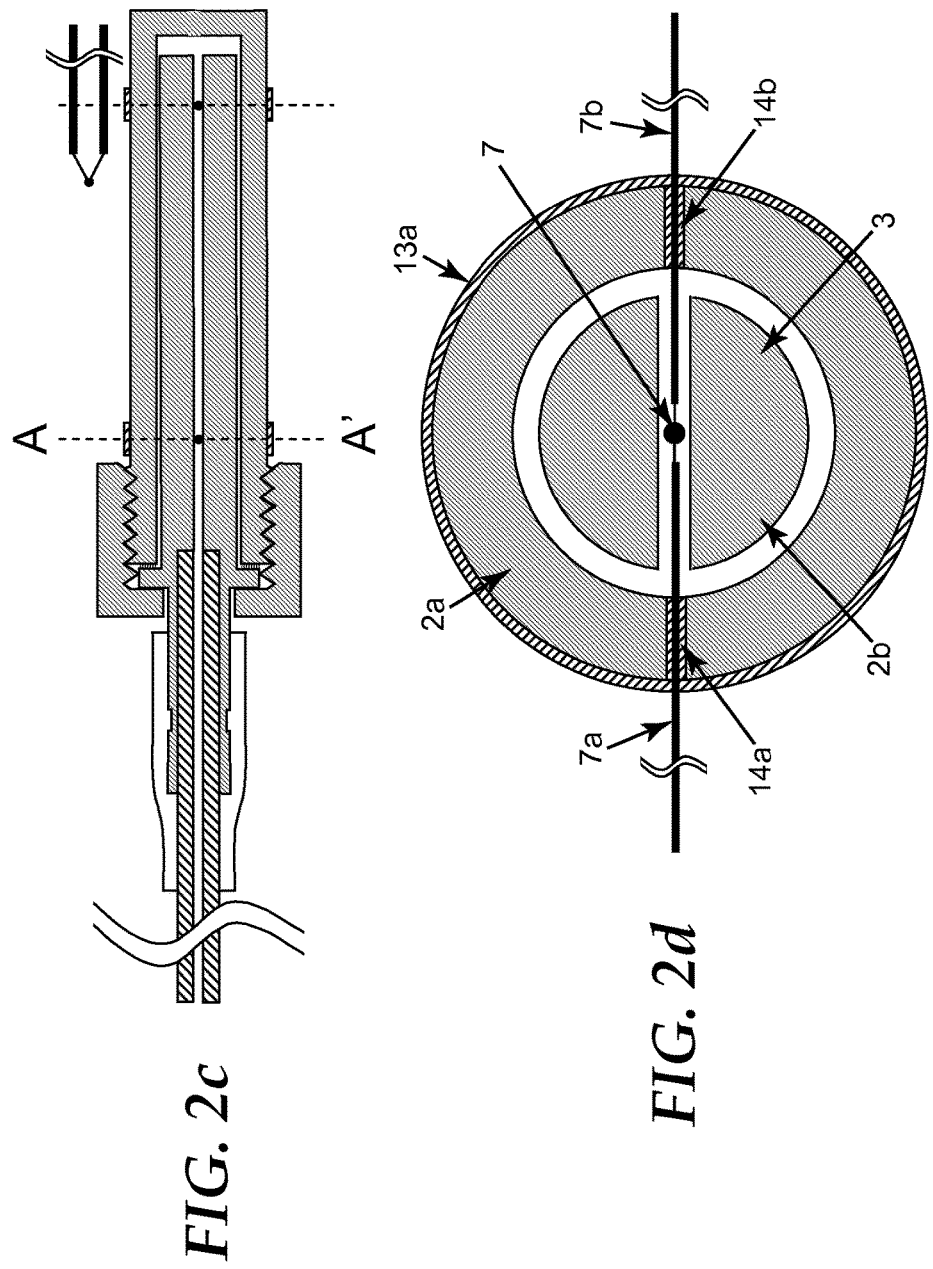

DEVICE AND METHOD FOR DETERMINING STERILIZATION CONDITIONS

CROSS REFERENCE TO RELATED APPLICATIONS

This application is a national stage filing under 35 U.S.C. 371 of PCT/US2011/051878, filed Sept. 16, 2011, which claims priority to United Kingdom Application No. 1015526.5, filed Sept. 17, 2010, the disclosures of which are incorporated by reference in their entirety herein.

TECHNICAL FIELD

The present disclosure relates to devices and methods for determining sterilization conditions.

BACKGROUND

Any steam sterilization process used to sterilize medical and hospital equipment cannot be effective unless the steam sterilant has been in contact with all surfaces of the materials being sterilized for the proper combination of time, temperature, and steam quality. In steam sterilizers, such as pre-vacuum steam sterilizers and gravity displacement steam sterilizers, the process of sterilization is conducted in three main phases. In the first phase, air is removed, including air trapped within any porous materials being processed. The second phase is a sterilizing stage, in which the load is subjected to steam under pressure for a recognized, predetermined combination of time and temperature to effect sterilization. The third phase is a drying phase in which condensation formed during the first two phases is removed by evacuating the chamber.

Air removal from the sterilization chamber may be achieved in a number of ways. For example, in a gravity displacement steam sterilizer, the principle of gravity displacement is utilized, in which steam entering at the top gradually displaces the air through a valve in the base of the chamber. Alternatively, in a pre-vacuum steam sterilizer, air is removed forcibly by deep evacuation of the chamber or by a combination of evacuation and steam injection at either subatmospheric and/or superatmospheric pressures.

Any air that is not removed from the sterilizer during the air removal phase of the cycle or which leaks into the sterilizer during a subatmospheric pressure stage due to faulty gaskets, valves or seals may form air pockets within any porous materials present. These air pockets will create a barrier to steam penetration, thereby preventing adequate sterilizing conditions being achieved for all surfaces of the materials being sterilized during the sterilizing phase. This is particularly true when porous materials such as hospital linens or fabrics are being sterilized since the air pockets prohibit the steam from reaching the interior layers of such materials. Other particularly problematic objects to be sterilized are medical devices having elongated and/or long hollow spaces, e.g. tubing, catheters, syringe needles, which are not easily penetrated by the steam. As a result, proper sterilization may not occur. Therefore, there is a need for a device and a method for determining the efficacy of sterilization cycles in sterilizers which operate by detecting whether there has been sufficient sterilant penetration.

SUMMARY

One commonly used procedure for evaluating the effectiveness of air removal during the air removal phase of a porous load sterilization cycle is known as the Bowie-Dick test. The typical Bowie-Dick test pack essentially consists of a stack of freshly laundered towels folded to a specific size. A chemical indicator sheet is then placed in the center of the pack. If the air removal within the sterilizer is insufficient, an air pocket will form in the center of the pack thereby preventing steam from contacting the steam sensitive chemical indicator sheet. The presence of the air pocket will be recorded by the failure of the indicator to undergo complete or uniform colour change, indicative of adequate air removal. Although the Bowie-Dick type test is generally recognized as an adequate procedure for determining the efficacy of the air removal stage of pre-vacuum sterilizers, it stills presents many disadvantages. Since the test pack is not preassembled, it must be constructed every time the procedure is used to monitor sterilizer performance. The testing procedure may be somewhat inconsistent because varying factors, such as laundering, pre-humidification, towel thickness and wear, and the number of towels used, alter the test results. Further, the preparation, assembly and use of the towel pack is time consuming and cumbersome. Therefore, alternative Bowie Dick test packs have been developed to overcome these limitations.

An example of an alternative Bowie-Dick test pack is described in EP 0 419 282 (Marvin and Kirckof) which describes a disposable test pack for steam or gas sterilizers. The test pack includes a container having top and bottom walls with a porous packing material disposed within the container. The packing material challenges the penetration of the sterilant by providing a restricted pathway which acts to impede the flow of the sterilant through the test pack.

Parametric monitoring has been used to either monitor or control a sterilization cycle. For example, in U.S. Pat. No. 4,865,814 (Childress) an automatic sterilizer is disclosed which includes a microprocessor which monitors both the temperature and pressure levels inside the sterilization chamber and controls a heater to allow both pressure and temperature to reach predetermined levels before starting a timer. Once the timer is started, it is stopped if the pressure or temperature levels drop below a predetermined minimum.

Sterilization criteria for steam sterilizers are often defined by requiring items to be sterilized to be subjected to a high quality steam at a given temperature for a predetermined period of time. Since it is known that the pressure and temperature variables of saturated steam are dependent variables when saturated steam is enclosed in a sealed chamber, monitoring of these two variables may ensure that proper conditions are maintained during the sterilization cycle.

Although it is desirable to monitor environmental conditions within the sterilization chamber itself, it is even more desirable to be able to monitor the environmental conditions and determine the efficacy of a sterilization cycle within or at the center of the actual load (not a test pack) being sterilized.

While external monitoring may be used, it is further desirable to have a self contained monitoring unit, which avoids having to run wiring into the sterilization chamber, thereby potentially breaching the integrity of the chamber.

U.S. Pat. No. 3,982,893 (Joslyn) discloses a sterilizer control apparatus which includes a housing which can be placed within a load to be sterilized, sensor means on the exterior of a wall of the housing to continuously monitors environmental conditions of the load, including at least humidity and temperature. The apparatus includes a RF generator in the housing which generates a signal and transmits it to an antenna placed in the sterilization chamber which is wired to an outside control means which controls the operation of the sterilizer. Thus, the apparatus of U.S. Pat. No. 3,982,893 provides a means for controlling the operation of the sterilizer rather than testing the efficacy of the sterilization cycle by monitoring the humidity and temperature at the center of the load.

The devices used today to test the efficacy of sterilizers typically employ biological and/or chemical indicators. The Bowie-Dick test is an example of a chemical indicator test typically carried out at the start of testing each working day in order to determine the efficacy of the air removal stage of the cycle. The test is designed to detect the presence of residual air within the sterilization chamber due to leaks, failed gaskets or valves or the ingress of noncondensible gases present in the steam supply, all of which prevent adequate steam penetration into the porous mass constituting the test pack. Chemical indicator test sheets undergo a visible change from either one distinct colour to another, for example, from an initial white to a final black colour, upon exposure to the sterilization process. The consequence of inadequate steam penetration is a non-uniform colour development across the surface of the chemical indicator test sheet. Chemical indicators, however, can be difficult to interpret, depending on the state of the colour change.

Biological indicator systems provide information on the adequacy of the sterilization stage of the cycle. Biological indicator test systems employ living spores which are subjected to a sterilization cycle. After the cycle, the spores are incubated and the system detects if there is any growth. If there is no growth, it indicates that the sterilization process has been effective. Thus, biological indicators can determine whether conditions for sterilization were present, but the length of time to obtain results due to the incubation period is often at least 24 hours. Therefore, biological indicator systems are often used in conjunction with chemical indicators because the colour change of the chemical indicators provides an instant result. Further, by using both chemical and biological indicators, information on both the adequacy of the air removal stage and the sterilization stage is provided.

Parametric monitoring has advantages over chemical or biological indicators because results could be obtained instantaneously and the results could be used to provide a clear pass/fail decision. In addition detailed data may be obtained from parametric monitoring that allows for further analysis into the performance of the sterilizer.

EP 1 230 936 (van Doornmalen and Verschueren) describes a method and a device for determining the sterilization conditions for surface sterilization with a sterilant adjacent a reference surface which is in communication with a sterilization space, the sterilant having only limited access to the reference surface. The method comprises the step of generating an electronic signal from which the sterilization conditions adjacent the reference surface can be derived. The reference surface can be arranged in a reference space.

The device shown in FIG. 1 of EP 1 230 936 is described in EP 1 230 936 as follows: The device comprises a reference chamber in the form of a narrow lumen. The lumen can be placed in a sterilization space, in which a sterilant, such as steam, is introduced. The lumen is closed at one end; the terminal inner wall is provided with a transducer, with the aid of which the temperature and the degree of saturation of the sterilant adjacent the transducer can be determined The geometry of the lumen is such that a sterilant, with respect to the other parts of the sterilization space, has relatively difficult access to the transducer. The lumen is formed by a tube of about 1.5 m, having an outside diameter of 3 mm and an inside diameter of 2 mm. The transducer comprises a temperature sensor, which can produce an electronic signal with the aid of which the sterilization conditions adjacent the wall can be determined Further, the lumen is provided with partially thermally insulated walls adjacent the closed end. The signals coming from the sensor are coupled via a signal line to a processing unit. The unit is also in communication with a pressure sensor, which can measure the pressure in the sterilization space. The processing unit, by relating the measured temperature to the measured pressure, can determine the degree of saturation of the sterilant adjacent the temperature sensor.

The device shown in FIG. 2 of EP 1 230 936 is described in EP 1 230 936 as follows: The embodiment can be placed as one whole in a sterilization space, and function as a test appliance, with the aid of which the process conditions during sterilization can be assessed. To that end, the appliance comprises a chamber, in which an electronic temperature sensor is arranged. The chamber comprises a coupling element, for instance in the form of a screw coupling, so that it can be connected with bodies having a geometry corresponding to objects to be sterilized, e.g. represented in the form of a hollow lumen. The temperature sensor is thermally insulated with respect to the sterilization space by means of thermally insulating walls, and connected with an electronic processing unit. The unit is heat-resistant and comprises a further temperature sensor, for measuring the temperature in the sterilization space, and a pressure sensor for measuring the pressure in the sterilization space. The processing unit relates the temperature measured by the sensor in the chamber to the pressure measured by the pressure sensor and to the temperature measured by the temperature sensor in the sterilization space, and derives therefrom the degree of saturation of the sterilant in the chamber. Also, the degree of saturation of the sterilant in the sterilization space is determined, by relating the temperature measured by the sensor to the measured pressure. In the event of a predetermined deviation of the sterilization conditions determined in the chamber, with respect to the conditions determined in the sterilization space, an indicator lamp, for instance an LED, can start to blink red, to indicate that a sterilization is not proceeding properly or has not proceeded properly. If such a deviation does not occur, the LED can show a green signal light, indicating that sterilization is correctly performed.

We have, however, found that the method and devices of the type described in EP 1 230 936 may not lead to proper results. The task of properly determining whether or not sterilization conditions have been met under certain circumstances is rather complex. We have found that it does not suffice that a specific temperature is achieved at or on the object to be sterilized. Rather, for effective steam sterilization, in order to eliminate all or substantially all microorganisms, a minimum heat transfer has to take place. The larger the saturation of the steam the better is the heat transfer taking place from the steam to the surface of the object to be sterilized. Therefore, measuring the temperature even in "a reference chamber in the form of a narrow lumen" as suggested by EP 1 230 936 does not always guarantee that desired sterilization conditions are met. Moreover, we have found that commercial appliances of the type described in EP 1 230 936 in some instances gave false passes seemingly as a result of higher temperature readings inside the test appliance than actual, which, without wanting to bound to a particular theory, seems to be due to the internal sensor being placed in contact with an interior wall of the appliance and the fact that all materials possess at some level thermal conductivity and/or heat up.

It is therefore desirable to provide a device and a method for determining sterilization conditions within a sterilization chamber which provides more reliable and more accurate results than devices and methods known in the prior art.

In one aspect of the present disclosure there is provided an improved device for determining sterilization conditions within a sterilization chamber. The device comprises an elongate tube to be placed within said sterilization chamber, said tube having a tube wall and a cavity therein and being open at one end and closed at the other end thereof. The device further comprises at least two temperature sensors within the cavity of the elongate tube, the at least two temperature sensors being spaced apart from each other along the length of the elongate tube by a predetermined distance and being spaced apart from the interior wall of the elongate tube.

Devices according to the present disclosure providing at least two temperature sensors in the cavity of the elongate tube along its length and having them spaced apart from the interior wall of the elongate tube improve accuracy and reliability of the decision-making whether or not sterilization conditions are met within the sterilization chamber. By spacing the at least two temperature sensors apart from the interior wall of the elongate tube, heat transfer at the wall may be advantageously minimized, thus facilitating provision of accurate temperature measurement. By measuring the temperature at two or more positions spaced apart along the length of the elongated tube, allows one to gather information regarding the temperature transfer and the temperature transport as well as the temperature gradient within the elongate tube. While a single temperature sensor within the elongate tube provides information whether or not a predetermined temperature is reached at a specific location within the elongate tube, two or more temperature sensors spaced apart from each other provide additional information regarding the velocity or rate of the temperature increase within the elongate tube. This information may be utilized to more reliably determine whether or not sterilization conditions are met within the sterilization chamber. Moreover we have found that a determination of a temperature gradient along the length of the elongate tube allows for a desirable assessment of the air/steam mixture within and along the elongate tube as well as the amount of steam present/the amount of air remaining within and along the elongate tube, since the higher the amount of steam there is in a air/steam mixture, the higher the temperature. Devices described herein using at least two temperature sensors (e.g. thermocouples) spaced apart from each other along the length of the elongate tube at predetermined distance and spaced from the interior wall of the elongate tube allow one to make an desirably accurate assessment of the air/steam gradient and thus a desirably reliable determination of sterilization conditions allowing for an improved assessment of the efficacy of the sterilization cycle.

According to some embodiments, the at least two temperature sensors are arranged to be substantially thermally disconnected from the exterior of the elongate tube except through the opening at the open end of the elongate tube. Thus, it is further facilitated that the temperature increase which is measured by the at least two temperature sensors within the elongate tube is essentially only caused by a heat transfer through the passageway of the elongate tube and that the potential of heat transfer not through the passageway, lateral heat transfer from the exterior of the elongate tube, e.g. through the wall of the elongate tube to the temperature sensors is yet further minimized In this context, the term "thermally disconnected" is to be understood in such a manner that there is no thermal bridge from the exterior of the elongate tube to the temperature sensors. "Substantially thermally disconnected" means that lateral heat transfer during a standard sterilization procedure amounts to less than 50%, preferably less than 40%, more preferably less than 30% and most preferably less than 25% in terms of, percentage of signal to noise ratio, $((Q_{PMax}+Q_L)/(Q_{PMin}+Q_L)) \times 100\%$ where $Q_P$ is heat transfer through the passageway of the elongate tube to the temperature sensors and $Q_L$ laternal heat transfer (i.e. heat transfer not through the passageway, e.g. through the wall, through wires, etc.) to the temperature sensors.

Devices may desirably comprises a processor adapted to determine, on the basis of the temperatures measured by the at least two temperature sensors within said tube in conjunction with a reference temperature, whether predetermined sterilization conditions are met within said sterilization chamber. Reference temperature is generally understood to be the unchallenged temperature within the sterilization chamber. Accordingly the reference temperature is advantageously determined at a location within said sterilization chamber but external to the elongate tube. The device preferably further comprises a temperature sensor external to the elongate tube and/or a pressure sensor external to the elongate tube. The reference temperature may either be directly measured by said temperature sensor external to the tube or calculated on the basis of a pressure measured by said pressure sensor external to the tube.

It is preferred that the at least two temperature sensors within the elongate tube each comprise a thermocouple, preferably a type T or type R or type S or type B thermocouple. Of course, other sensor means to measure the temperature within the elongate tube may be utilized as well. However, the aforementioned thermocouples are advantageous since they have a small thermal mass and provide reliable results.

Desirably, the wall of the elongate tube comprises at least two passages therethrough and each thermocouple comprises two wires, each wire extending through a passage in the tube wall. It is preferred that the elongate tube is cylindrical and that the wires extend radially through the tube and the ends of the wires are connected with each other at a location essentially on the central axis (along the length) of the tube to form a thermocouple. Such a symmetric arrangement further minimizes the heat transfer from the wall of the tube to the thermocouple, thus further enhancing the provision of reliable and accurate results. It is further preferred that the interior of each passage together with each wire passing therethrough is sealed with a sealing material in order to minimize thermal connection of the thermocouples to the exterior of the elongate tube. Suitable sealing materials are, e.g., siloxane, in particular a polysiloxane, more particularly vinyl polysiloxane, as well as other materials known to have good temperature insulation properties. In order to yet further optimize the thermal insulation it is preferred that the external opening of each passage together with each wire passing therethrough is covered with a sealing collar. Suitable materials for the sealing collar are inter alia the sealing materials mentioned above. It is advantageous to use wires having a diameter of equal to or less than 0.4 mm, preferably equal to or less than 0.35 mm, more preferably equal to or less than 0.2 mm. The smaller the diameter of the wire of the thermocouple, generally the smaller is the potential for any heat transfer from the exterior of the elongate tube through the wire towards the location of measurement within the tube.

In preferred embodiments, devices may comprise three, four, five, six or more temperature sensors within the elongate tube. Preferably, these temperature sensors are all spaced apart from each other along the length of the elongate tube by predetermined distances, more preferably equally spaced from each other.

Temperature sensors within the elongate tube may be desirably spaced apart, preferably with a distance from 5 mm up to and including 40 mm, more preferably from 10 mm up to and including 30 mm.

The overall length of an elongate tube depends on how many temperature sensors are employed and the selected spacing between the sensors. Generally for an elongate tube including two sensors, an overall length of at least 40 mm would be desirable.

It is generally favourable in the evaluation the air/steam gradient within the elongate tube to locate at least one of the temperature sensors near the closed end of the elongate tube. At least one of the temperature sensors may be desirably positioned at a distance from the interior wall of the closed end in the range 0.5 to 6 times the radius of inner diameter of elongate tube, more desirable 1 to 4 times the radius of inner diameter of elongate tube.

In a preferred embodiment of a device in accordance with the present disclosure, the elongate tube including the at least two temperature sensors is configured so that it can be coupled, more preferably releasably coupled, to an elongate lumen.

In another preferred embodiment of the device in accordance with the present disclosure, the elongate tube is coupled to an elongate lumen Such an elongate lumen may have a length of from about 1 m up to 3 m, in particular from about 1 m up to 2 m, more particular about 1.5 m.

The elongate tube and, if used, the elongate lumen may desirably have an inner diameter of 10 mm or less, preferably 8 mm or less, more preferably 6 mm or less, or even more preferably 4 mm or less and most preferably about 2 mm.

To avoid or minimize a potential of steam condensation within the elongate tube and, if used the elongate lumen, desirably the wall thickness along their length is not too thick. For example the use of a thick wall may result in a situation where the interior wall is cool (relative to the exterior) which may allow for the condensation of steam. As will be appreciated this could lead to disadvantageously incorrect temperature measurements and thus an incorrect assessment of the sterilization conditions. Accordingly the elongate tube and, if used, the elongate lumen may preferably have a wall thickness along the length of the elongate tube or elongate lumen, respectively, of 4 mm or less, more preferably 3 mm or less, even more preferably 2 mm or less, most preferably 2 mm down to and including 0.35 mm.

The present disclosure further provides in another aspect a method for determining sterilization conditions within a sterilization chamber. Methods in accordance with this aspect of the present disclosure preferably utilize devices as described herein. According to the method, a predetermined sterilization protocol is performed. During said protocol at least a first and a second temperature at first and second locations within an elongate tube situated within said sterilization chamber, is measured. Furthermore, a reference temperature at a location within said sterilization chamber and external to the elongate tube during said protocol is determined. Finally, it is determined, on the basis of at least the first and second temperatures and the reference temperature, whether predetermined sterilization conditions are met within said sterilization chamber.

The elongate tube may be either fixedly situated within the sterilization chamber or non-fixedly situated within the sterilization chamber (i.e. it can be put into and taken out the chamber), favourably it is non-fixedly situated. Desirably the elongate tube is placed into the sterilization chamber prior to the start of sterilization protocol performance.

Any sterilization protocol known in the art may be utilized. In principle, methods described herein for determining sterilization conditions within a sterilization chamber may be adapted to any sterilization protocol as long as this protocol is well-defined and predetermined.

The reference temperature is preferably determined either by directly measuring during the protocol a temperature at a location within said sterilization chamber, but external to the elongate tube or by calculating said reference temperature on the basis of a pressure measured during the protocol at a location within said sterilization chamber, but external to the elongate tube. If the reference temperature is directly measured, the same type of temperature sensors as utilized for measuring the first and second temperatures may be used. If the reference temperature is calculated on the basis of a pressure measured within said sterilization chamber, any known pressure sensor may be used for determining the pressure. Preferred types of pressure sensors are, e.g., piezo-resistance type pressure sensors.

In preferred embodiments of methods described herein, the method further comprises measuring at least one further temperature during said protocol at least one further location within said elongate tube.

The measured first and second temperature, and if applicable, further temperatures plus the determined reference temperature may be utilized in different ways to determine whether predetermined sterilization conditions are met within said sterilization chamber. According to a preferred embodiment, it is determined on the basis of the difference between the first and second temperatures and, if applicable, said further temperature, whether predetermined sterilization conditions are met within said sterilization chamber. In addition, or alternatively, it may be determined on the basis of the temperature gradient within said elongate tube at one or more points of time during the protocol whether predetermined sterilization conditions are met within said sterilization chamber. For this determination the increase of the first and/or second and/or, if applicable, said further temperatures during a time interval during the predetermined protocol may be measured and utilized. For an optimized analysis, several (spatial) differences and/or (temporal) gradients may be calculated in order to determine whether the predetermined sterilization conditions are met.

Temperatures may be measured within the elongate tube using any suitable technique for measuring a temperature. As outlined above, it is particularly advantageous to use thermocouples for measuring the first and second temperatures. Yet, any other technique which the temperatures within the elongate tube to be measured and providing sufficiently precise results as desired and/or needed may be used.

As indicated above it is favourable that temperature measurement within the elongate tube be done in a manner such that measured temperatures are substantially unaffected by lateral heat, e.g. heat transfer through the wall of the elongate tube.

Desirably, temperatures are sensed and measured at locations, which are spaced apart from the interior wall of the elongate tube, for example along its central axis of the tube.

It is favourable that heat transfer to the locations within the elongate tube, the elongate tube generally, favourably being open at one end and closed at the other end thereof, essentially only takes place through the hollow cavity of the elongate tube, It is desirable that said first, second, and if applicable, further locations within the elongate tube are substantially thermally disconnected from the exterior of the elongate tube except through the opening at the open end of the elongate tube. Favourably at least one of these locations is located near the closed end of the tube. Favourably at least one of the locations within the elongate tube is located at a distance from the interior wall of the closed end in the range 0.5 to 6 times the radius of inner diameter of elongate tube, in particular in the range 1 to 4 times the radius of inner diameter of elongate tube.

Locations at which temperatures are measured within the elongate tube are desirably spaced apart from each other along the length of the elongate tube by a predetermined distance. The spacing distance may be desirably between 5 mm and 40 mm, more desirably between 10 mm and 30 mm. If the temperature is measured at 3, 4, 5, 6 or more locations within the elongate tube, these locations are preferably equally spaced from each other.

Devices and methods in accordance with the present disclosure allow a decision whether or not predetermined sterilization conditions have been met with advantageous accuracy and reliability, in particular for hollow loads. Devices and methods described herein may be easily used in conjunction with any known sterilization protocol. Devices described herein are versatile since it may be placed in just about any kind of sterilization chamber and/or in chambers containing loads to be sterilized. Furthermore, devices described herein may be advantageous configured and arranged as a module that may be releasably coupled to different types of elongate lumens, the selection of the particular elongate lumen depending on the specific load to be sterilized and/or sterilization conditions.

BRIEF DESCRIPTION OF DRAWINGS

The present disclosure is further described with reference to the following Figures.

FIGS. 2A to C show schematic and, in part, partial diagrams of an exemplary embodiment of a device in accordance to the present disclosure. FIG. 2D provides a schematic cross-sectional diagram along plane A-A' shown in FIG. 2C.

DETAILED DESCRIPTION (Similar parts, elements, etc. will be referred to with the same reference numbers.)

An important aspect for successful sterilization is the ability of the sterilizer and process to reach all surfaces for the goods to be sterilized and expose them for an adequate amount of time with good quality steam (100% dry and saturated). Methods for monitoring sterilization conditions and which in turn may allow for an assessment of efficacy of sterilization often include posing a challenge for steam to reach a surface which is difficult to access, for example by utilizing a "challenge" that is porous or hollow in nature.

Test methods, Bowie Dick test and alternative Bowie Dick tests, for using a porous load as a challenge are described in various local and international standards (e.g., ISO 11140 parts 3, 4 and 5). A device and test method for hollow loads in small sterilizers (<70 litres) is described in EN-13060:2004 and EN 867-5:2001. A test method for hollow loads in large sterilizers (≥70 litres) is not fixed in an international standard yet.

Figure 1:
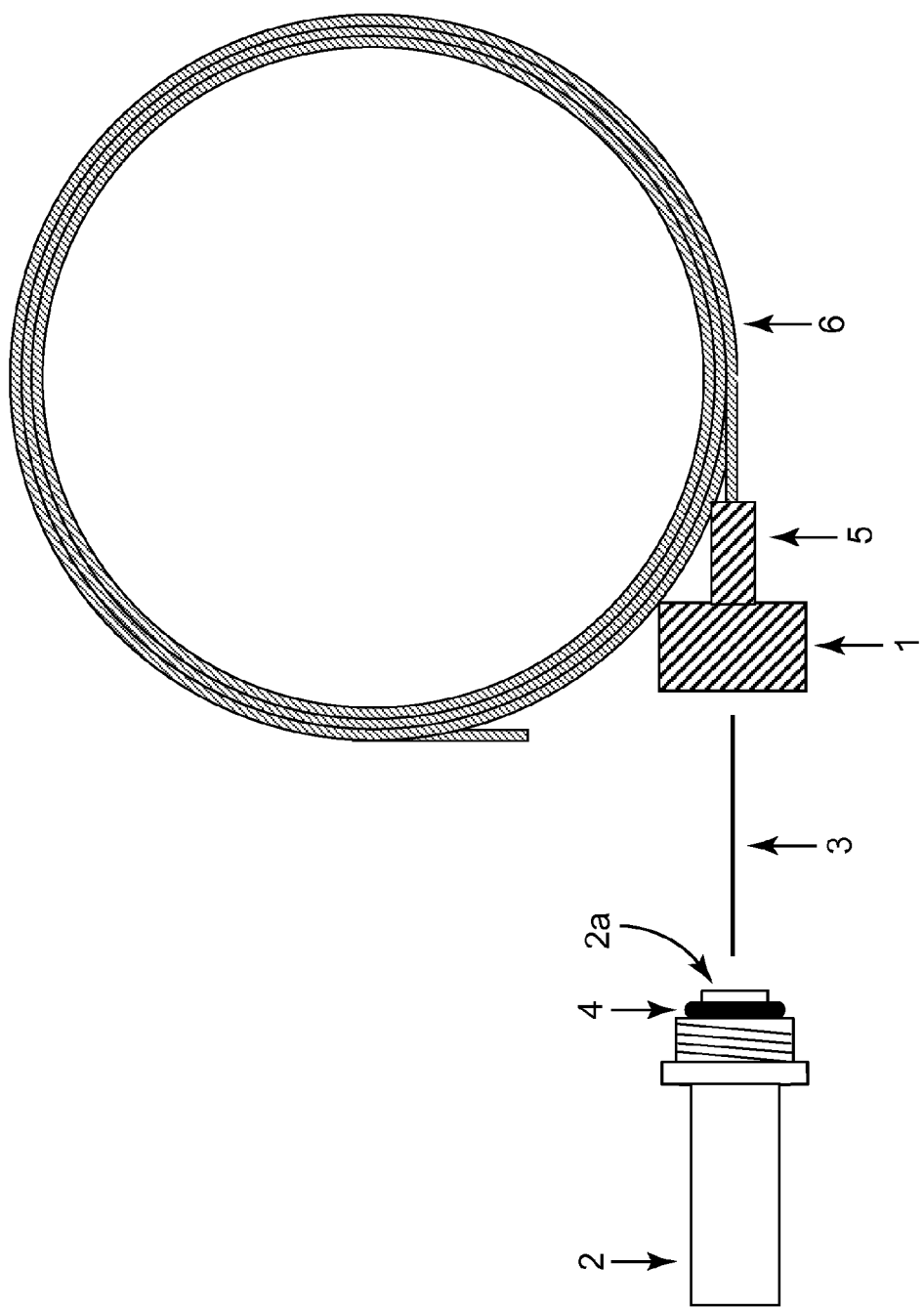
FIG. 1 shows a schematic illustration of a process challenge device and chemical indicator system similar to that described in EN-13060:2004.

An example process challenge device and chemical indicator system for hollow loads in small sterilizers is described in EN-13060:2004, and a schematic illustration of such a device in shown FIG. 1. The device includes a capsule (2) into which a chemical indicator system, a chemical indicator (3) is loaded through a slit-like opening (not visible, 2a) in the capsule. A coiled narrow hose or tubing (6) is connected to the capsule (2) via a nut (1) that is screwed onto threading provided on the exterior of the capsule. A tight sealing is generally facilitated by means of an O-ring (4), and the coiled tubing is generally attached to the nut (1) via a connector (5). Capsules, nuts and coiled tubes are generally made of PTFE, connectors silicone and O-rings heat resistant elastomer.

As mentioned in the introduction the use of a chemical indicator can be difficult providing ambiguous color changes that can lead to false results and may thus introduce a false sense of safety for user and patient. In this regard, parametric monitoring using parametric process challenge devices described herein have advantages over chemical (or biological) indicators because results that can be obtained quickly and the results may allow an much more clear determination of whether the sterilization conditions are obtained. Parametric process challenge devices described herein are relatively simple to use and at the same time are desirably accurate and reliable. They can be used equally well in large or small sterilizer.

FIGS. 2A to D show schematic and, in part, partial diagrams of an exemplary embodiment of a device in accordance to the present disclosure. In the exemplary process challenge device illustrated in FIG. 2, at least two temperature sensors 7 and 8 are placed within the cavity of a cap or an elongate tube 2 (see e.g. FIG. 2A). As can be seen from FIG. 2 the elongate tube 2 typically has a tube wall and includes an open end as well as closed end at the other end of the elongate tube. The elongate tube is desirably made of a thermally insulating material, such as PTFE. The at least two temperature sensors 7 and 8 are spaced apart from each other along the length of the elongate tube 2 as well as spaced apart from the interior wall of the elongate tube. Favourably, the temperature sensors 7 and 8 are thermocouples, which each comprise two wires 7A, 7B and 8A, 8B of different materials soldered or welded together at the center axis of the elongate tube 2 as shown in FIG. 2A. For example, two wires suitable to form a type T 0.005 inch thermocouple may be inserted from opposite ends through a passage provided in the wall of the elongate tube 2. The wires may then be welded together such that their welding point is positioned centrally with respect to elongate tube 2. The wires are desirably sealed within insulation jackets except of course the necessary portion thereof to form the thermocouple (see FIG. 2A). A first thermocouple 8 is positioned near the closed end 10 of the elongate tube 2 while a second thermocouple 7 is spaced apart from the first thermocouple 8 along the length of the elongate tube by a predetermined distance. The thermocouples are connected to a data acquisition unit (not shown) and calibrated against a reference thermometer. The passages (two visible in FIG. 2D and labelled in FIG. 2D as 14a and 14b) of the thermocouple wires through the wall is desirably sealed with a thermally insulating material such as a siloxane, in particular a polysiloxane, more particularly a vinyl polysiloxane. (For ease in viewing, the wires are typically not shown in FIGS. 2B and C) Favourably the exterior openings of each passage are covered for example with a collar (13a and b) made of a thermally insulating material such as a siloxane, in particular a polysiloxane, more particularly a vinyl polysiloxane.

As can be appreciated from FIGS. 2B and C the elongate tube 2 of the exemplary embodiment is favourably provided with an extension 2b including an extending portion 2c, hence providing the elongate tube a desirable configuration and arrangement so that the elongate tube may be coupled, in particularly releaseably coupled, to an elongate lumen. The exterior coupling-extension 2c may be favourably coupled to an elongate lumen using for example a sealing-coupler 5 made of e.g. silicone. In FIGS. 2B and C it can be seen the elongate lumen may be provided in the form of a narrow tubing 6. In particular referring to FIGS. 2B and C the original portion 2a is slided over two plates of a extension support 3 such that the two thermocouples 7 and 8 are inserted in the opening between the plates and then the two portions 2a and 2b are connected via a nut 1 and threading provided on the exterior near the open end of the first portion 2a. Once the portions are connected and sealed as shown in the FIG. 2C the exemplary embodiment is complete, and as mentioned supra it may be further coupled to an elongate lumen, Desirable sealing between the two portions of the elongate tube is facilitated through the use of an O-ring 4. Like the first portion (2a) of the elongate tube, the extension is desirably made of a thermally insulating material, such as PTFE except for O-ring which is generally made of a heat resistant elastomer. FIG. 2D provides a cross section view at the plane A-A' shown in FIG. 2C; the view in FIG. 2D is rotated 90°. In the cross sectional view it is can be recognized that the thermocouple (7)) is favourably positioned on the central axis of the elongate tube "in space", and the wires (7a and 7b) themselves are jacketed and the passages (14a and b) are doubly sealed.

As represented in FIGS. 2B to C, the exemplary embodiment is provided with a temperature sensor, e.g. a thermocouple 12, mounted externally to the elongate tube which is suitable for measuring unchallenged temperature within the sterilization chamber (i.e. reference temperature).

When devices described herein are first introduced into the sterilization chamber, the passageway within the elongate tube (and for those favourable embodiments including an elongate lumen the passageway within the length of the elongate lumen and elongate tube) from the outside to the closed end of the elongate tube is filled with air. Typical steam sterilization processes include several pressure pulses (evacuation and steam admission) acting on the inside of the sterilization chamber. The processes vary from each other by the number of pulses, the pressure change rates and the nature of the pulses such as subatmospheric, transatmospheric and sub superatmospheric. Evidently, as the sterilization chamber is filled with good quality steam at a predetermined pressure, the passageway of the elongate tube (or, if applicable, the passageway of the elongate lumen and elongate tube) will not instantly filled with steam. Rather, an air/steam gradient is formed within the extended passageway where the portion near to the closed end will have a higher portion of air, while the portion near to the open end will have a higher portion of steam. And as the sterilization protocol continues and goes through to its last come-up pulse—ideally—the amount of steam within the passageway should increase so the amount of air near the closed end of the passageway will be nearly eliminated (i.e. nearly eliminate, complete elimination is not possible). In such an ideal situation, the slope of the temperature gradient along the elongate tube should approach zero and the determined temperature near/nearest to the closed end of the elongate tube should approach the reference temperature at its sterilization plateau (around 134° C.).

For the experiments reported infra and the results shown in FIGS. 3 to 8, an Example Device of the type as shown in FIG. 2C was used, including an elongate tube coupled via a silicone coupler (30 mm long) to narrow coiled tubing (PTFE, 1.5 m long, inner diameter 2 mm, outer diameter 3 mm) The elongate tube was made of PTFE, the first portion had a length of around 41 mm, inner diameter 6.6 mm, outer diameter 10.2 mm and a wall thickness at closed end of 2 mm. Two thermocouples (type T, wire diameter 0.127 mm) were located within the elongate tube, spaced apart at a distance of 23 mm and positioned on the central longitudinal axis of the elongate tube. The thermocouple near the closed end was at a distance of 10 mm to the closed end. Except for the portions needed to make the thermocouple the wires were in their standard insulating jackets. The wire through-passages were filled with vinyl-polysiloxane and the external openings were covered with vinyl-polysiloxane collars. After insertion of second extension portion the elongate tube the two thermcouples were located in a central slit (similar to that shown in FIG. 2D), opening 0.8 mm wide. A O-ring made of silicone was used. Also an external type T reference thermocouple (wire diameter 0.127 mm) was mounted on the exterior of the elongate tube.

In the following experiments whose results are shown in FIGS. 3 to 5 and 7 and 8, in each case before the start of experimentation with the Example Device, the relevant sterilization protocol to be used in the experiment with the sterilizer to be used (342 Liter) were pre-assessed and pre-proven to pass the Bowie Dick Test. In addition to this, the experiments of FIGS. 3, 7, and 8 used a standardized "pass" protocol as described in ISO 11140-4 Annex B, B1 or B2 or B3, respectively, while experiments of FIGS. 4 and 5 used a protocol that is even better than B1. So normally all of these sterilization protocols are to be considered to provide proper sterilization. The experiment whose results are shown in FIG. 6 is a standardized "fail" protocol as described in B1 and before experimentation with Example Device, the sterilizer with this protocol was pre-proven to fail the Bowie Dick Test.

Thereafter the Example Device was tested in the sterilizer with the sterilization protocol. FIGS. 3 to 8 show the results of these tests where 4 parameters are plotted: the pressure inside the sterilization chamber ("P.Chamber"), unchallenged temperature inside the sterilization chamber ("Exterior Sensor"), temperature measured with sensor near closed end of elongate tube ("Sensor near End") and temperature measured with sensor within elongate tube near the coiled tubing ("Sensor near Tube").

Figure 3A:
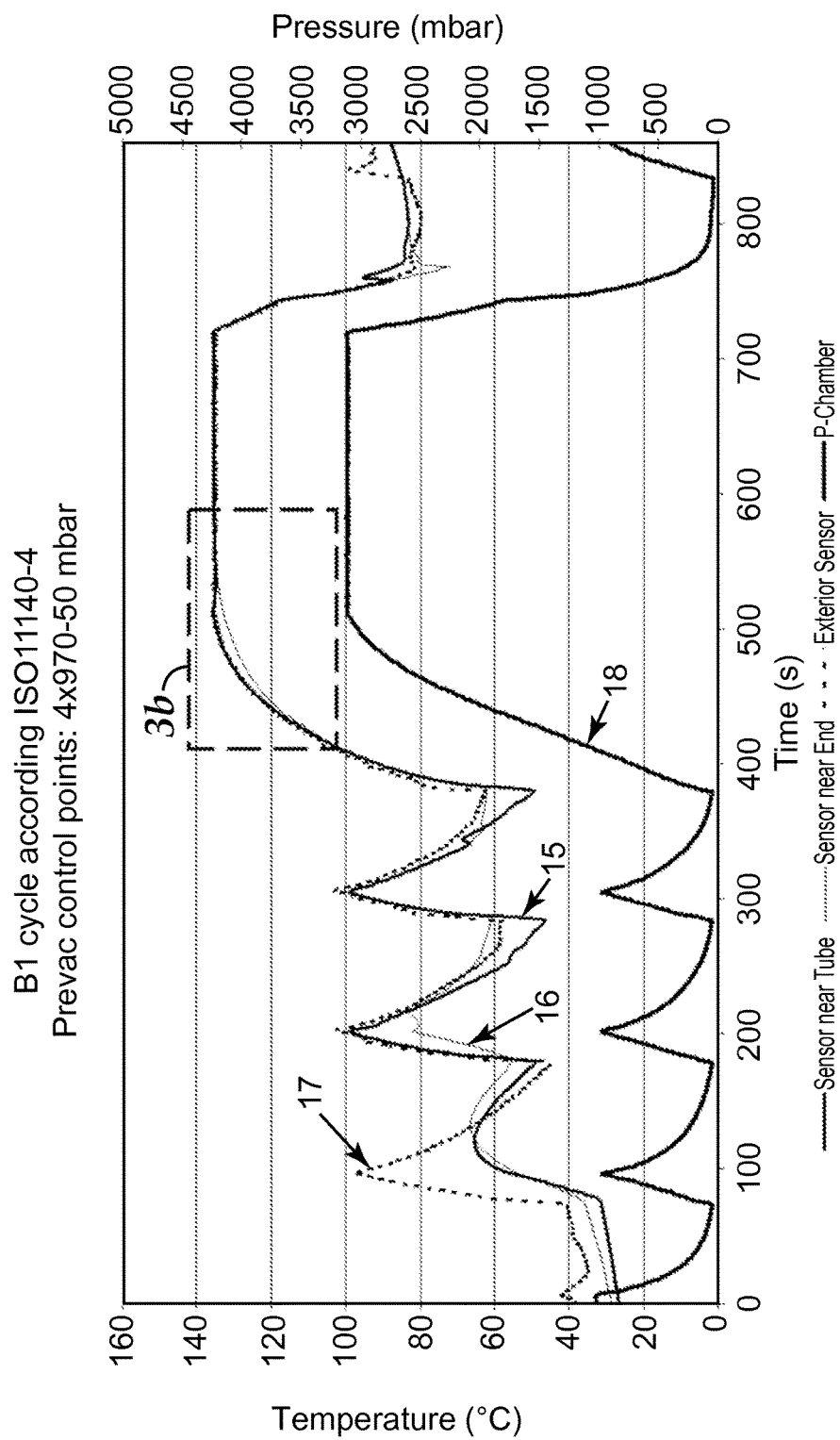
FIGS. 3 to 8 show graphs of temperatures and pressures measured in different sterilization protocols.

The title lines of FIGS. 3 to 8 list sterilization protocol and, if applicable test ID in ISO 11140-4. This is, for example, illustrated in the graph shown in FIG. 3, stating "B1 4×50-970". The sterilization protocol underlying the experiment whose results are shown in FIG. 3 comprises four pressure pulses at 970 mbar with subsequent evacuation phases at 50 mbar prior to last, come up pulse (i.e. the long steam admission pulse leading up to the sterilization plateau). The applied pressure is shown in curve 18 in FIG. 3. The temperature measured at three different positions during the process, namely: with a thermocouple (7 in FIG. 2) close to the open end of elongate tube 2, curve labelled 15 in FIG. 3; with a thermocouple (8 in FIG. 2) close to the closed end of the elongate tube 2, curve labelled 16 in FIG. 3; and with an external reference thermocouple mounted on the exterior of the elongate tube (12 in FIG. 2), thus inside the sterilization chamber, yet external to the challenge, curve labelled 17 in FIG. 3.

Figure 3B:
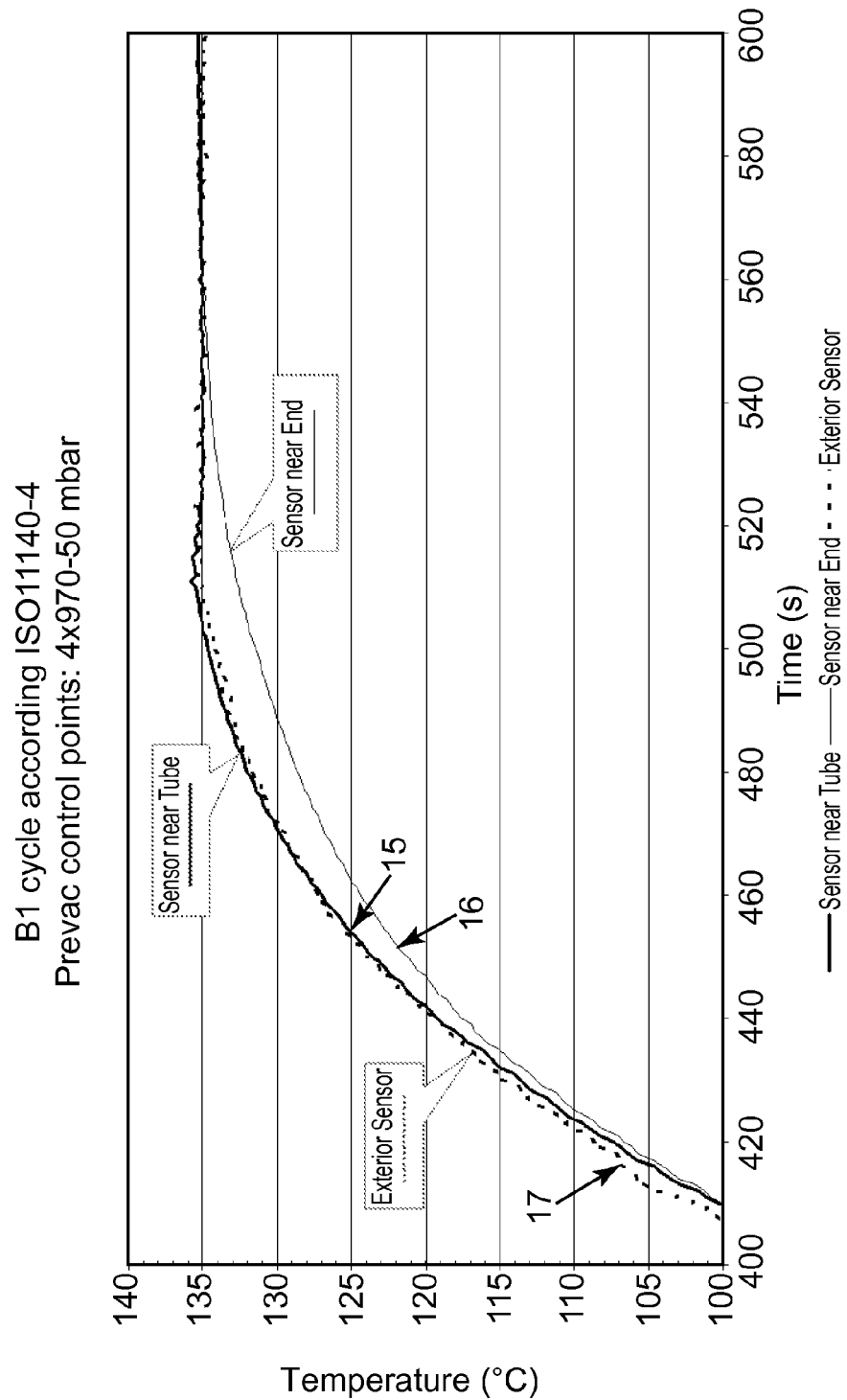

As clearly shown in FIG. 3, it takes four pulses until both measured temperatures within the elongate tube more or less follow the temperature exterior to the device. During the final pulse towards the sterilization temperature a reduced temperature rise of the thermocouple near the closed end of the elongate tube is visible in the marked region (see enlargement shown in FIG. 3*b*), and at the point in time when the reference temperature reaches 134° C. there is a difference between two challenged temperatures. This indicates that there is still some air present in challenge device, in particular near the closed end of elongate tube. This determination of remaining air suggests that this sterilization protocol may not lead to proper sterilization for hollow loads.

Figure 4A:
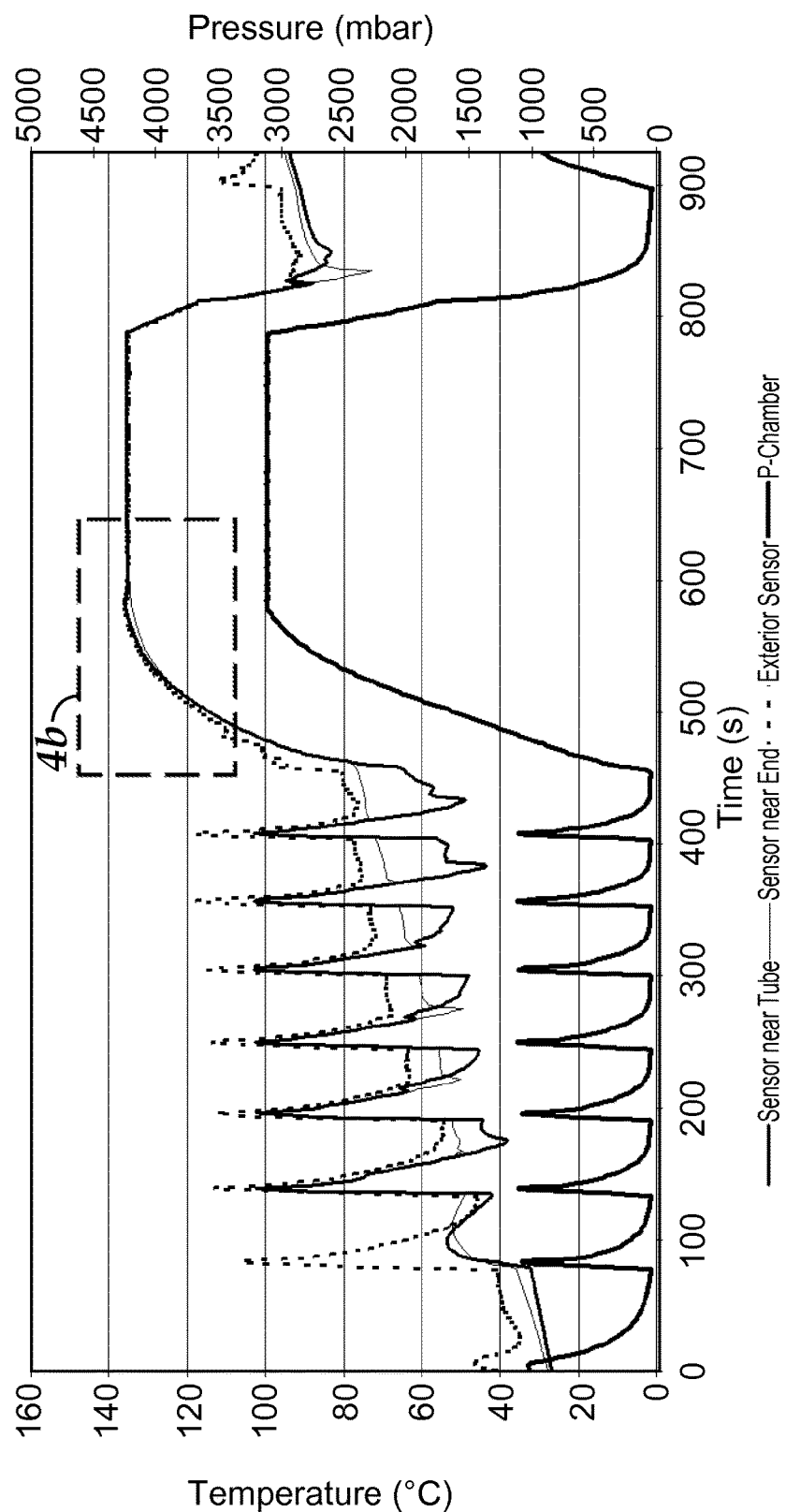
Figure 4B:
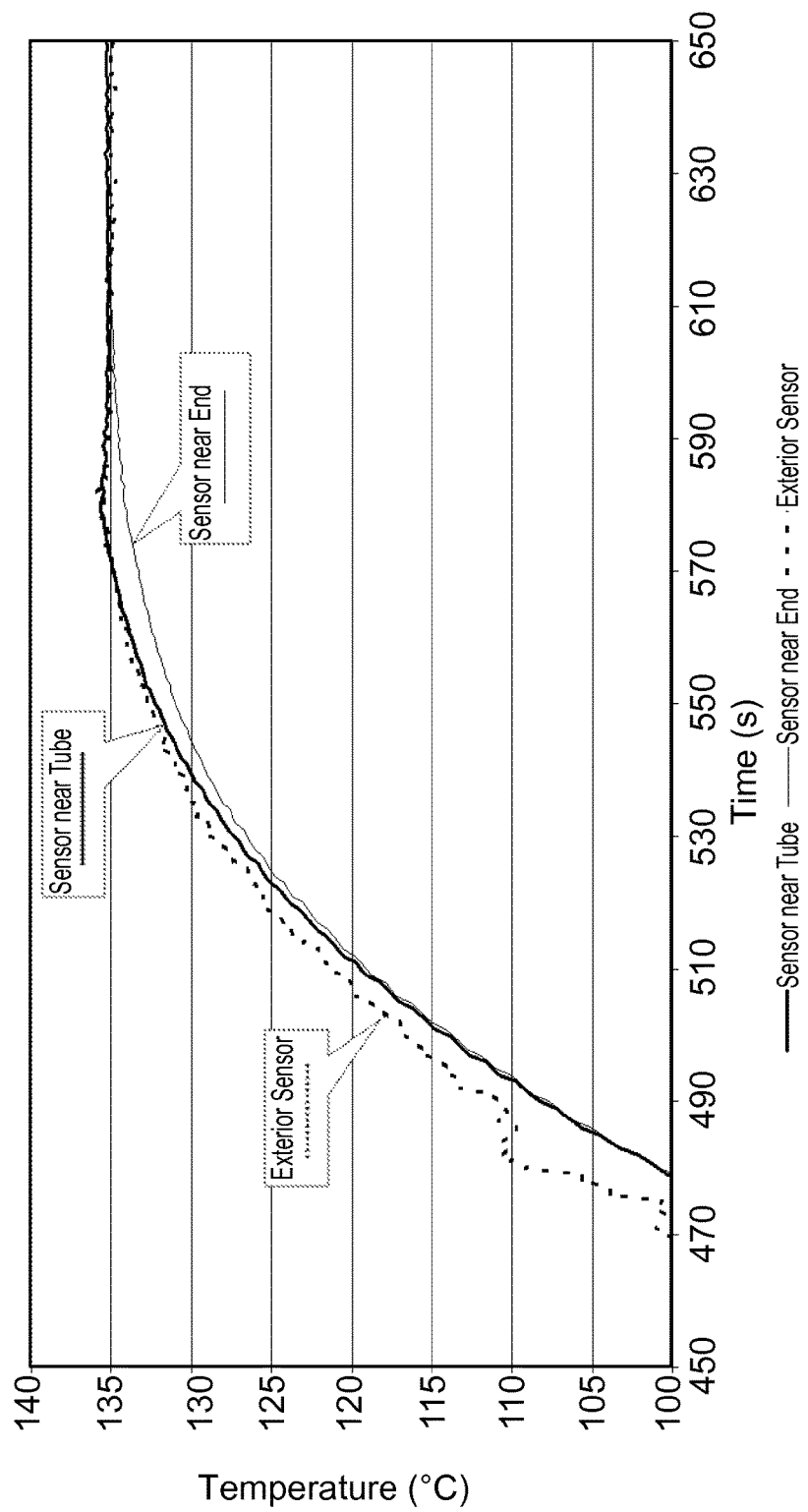

A better sterilization protocol was utilized in the experiment of FIG. 4. As shown in the Figure, the corresponding process consists of eight pulses at 970 mbar followed by evacuation phases at 40 mbar prior to the come up pulse. When the reference temperature just reaches 134° C., a less reduced temperature rise near the closed end of the elongate tube as well as a lower difference in the challenged temperatures are visible in the graph shown in FIG. 4. Hence compared to the previous test shown in FIG. 3 it can be concluded that there is less air present in the elongate tube. If an even better sterilization protocol is used, i.e. the number of pulses is further increased to 16 pulses at 40 to 970 mbar prior to come-up pulse (see FIG. 5), hardly any reduced temperature rise in temperature near the end of the elongate tube and hardly any difference to the challenged temperatures at the point time when the unchallenged reaches 134° C. exterior temperature can be recognized. Accordingly it can be concluded that there is even less air is present.

Figure 5A:
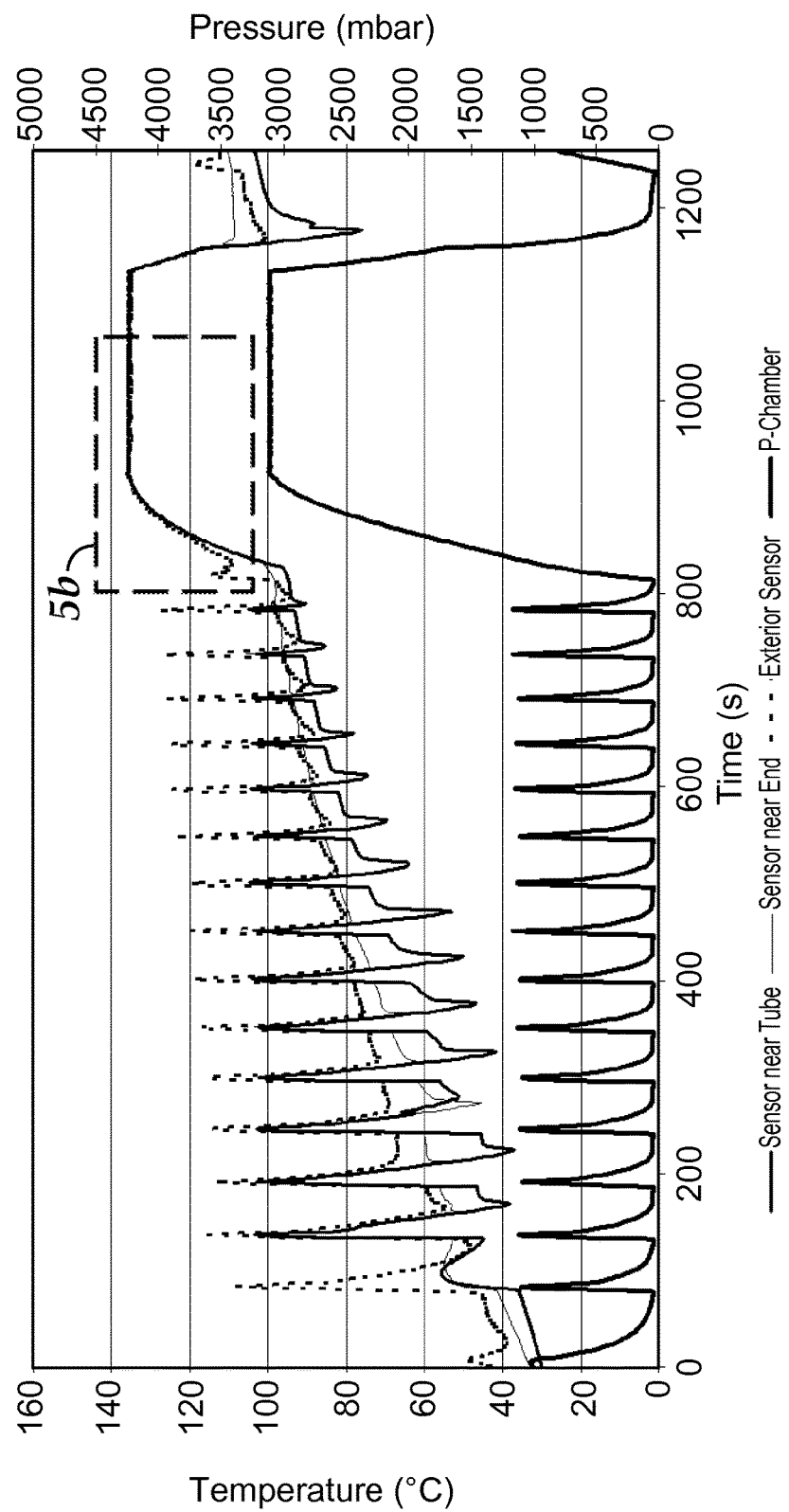
Figure 5B:
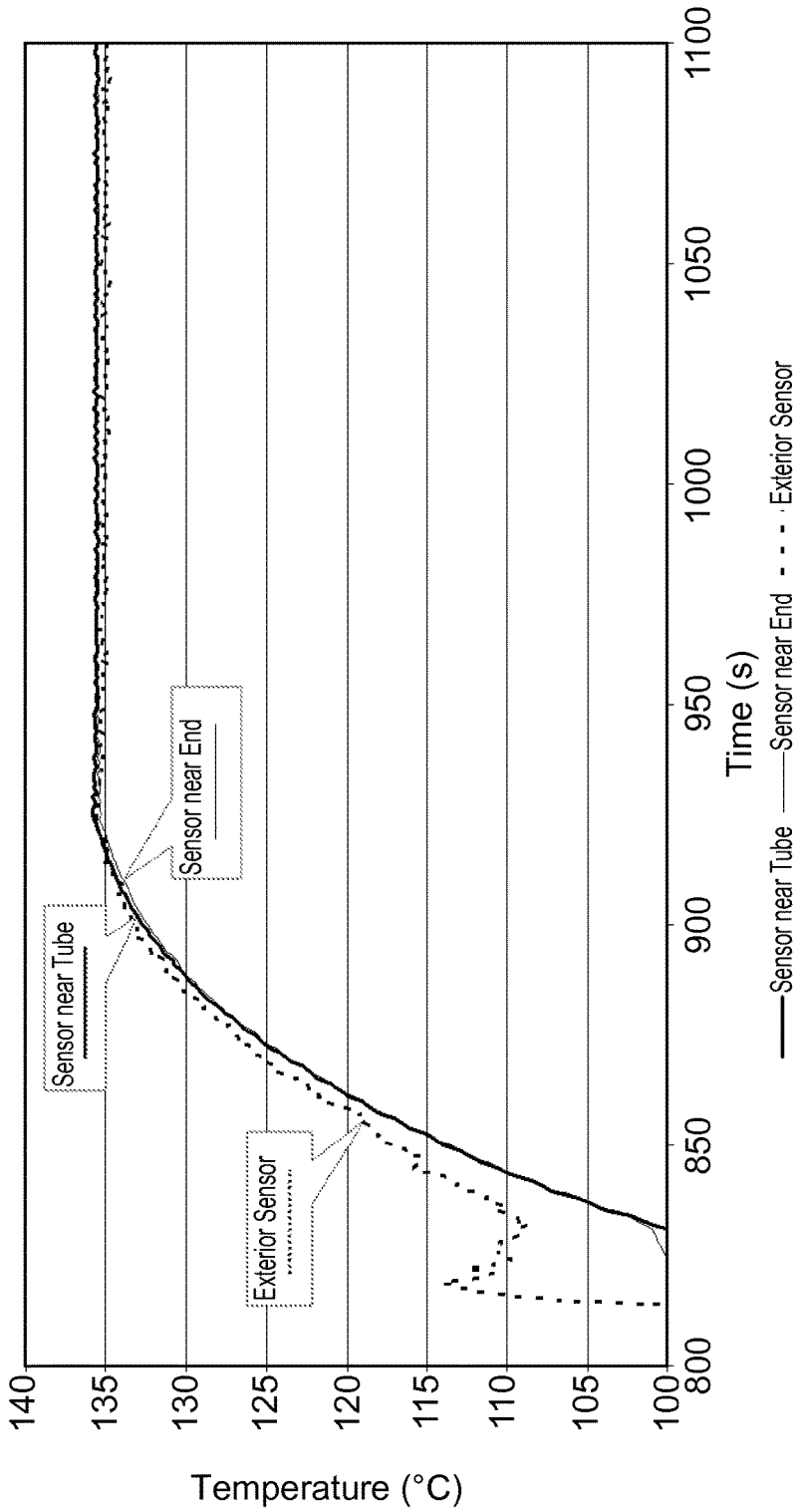
Figure 6:
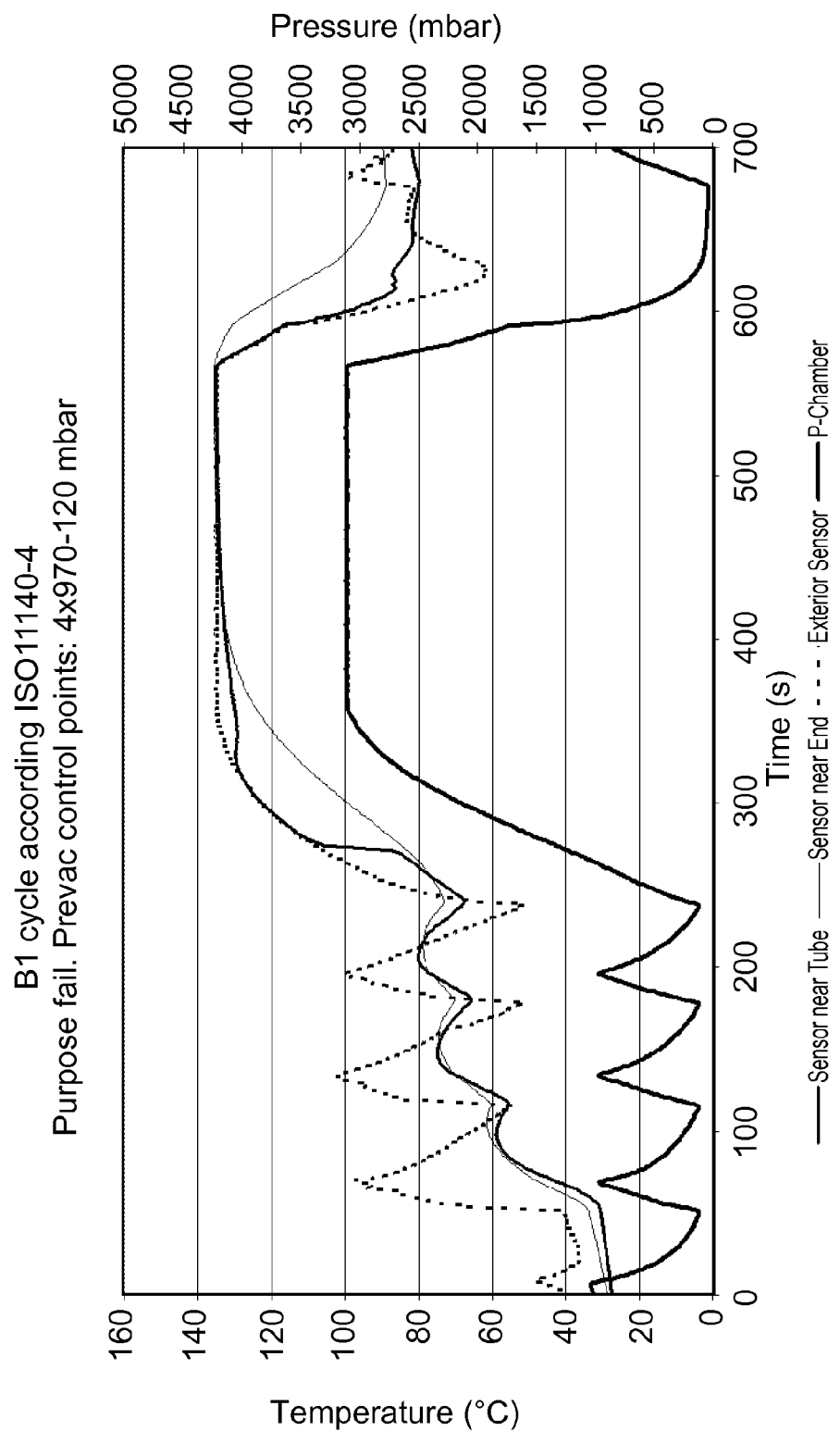

The experiments whose results are provided FIGS. 3 to 5 illustrate the advantageous sensitivity of devices described herein. In addition the experiments suggest that for hollow loads a sterilization protocol in accordance to that used in the experiment of FIG. 5 may be better for hollow loads than that of "B1 4×50-970"

As mentioned above, the sterilization protocol used in the experiment of FIG. 6 is a purposeful fail according to ISO 11140-4 B1, four pulses at 970 mbar followed by evacuation phases at 120 mbar. Monitoring this sterilization protocol with an Example Device shows a large reduced temperature rise at the sensor near the closed end of the elongate tube as can be easily seen in FIG. 6 without any enlargement. At the point in time when the reference temperature reaches 134° C., there is also quite a difference in temperature between the reference temperature and each of the challenged temperatures, even the one far from the closed end of the elongate tube. These observations are indicative of, a significant amount of air being still present in the elongate tube.

Figure 7A:
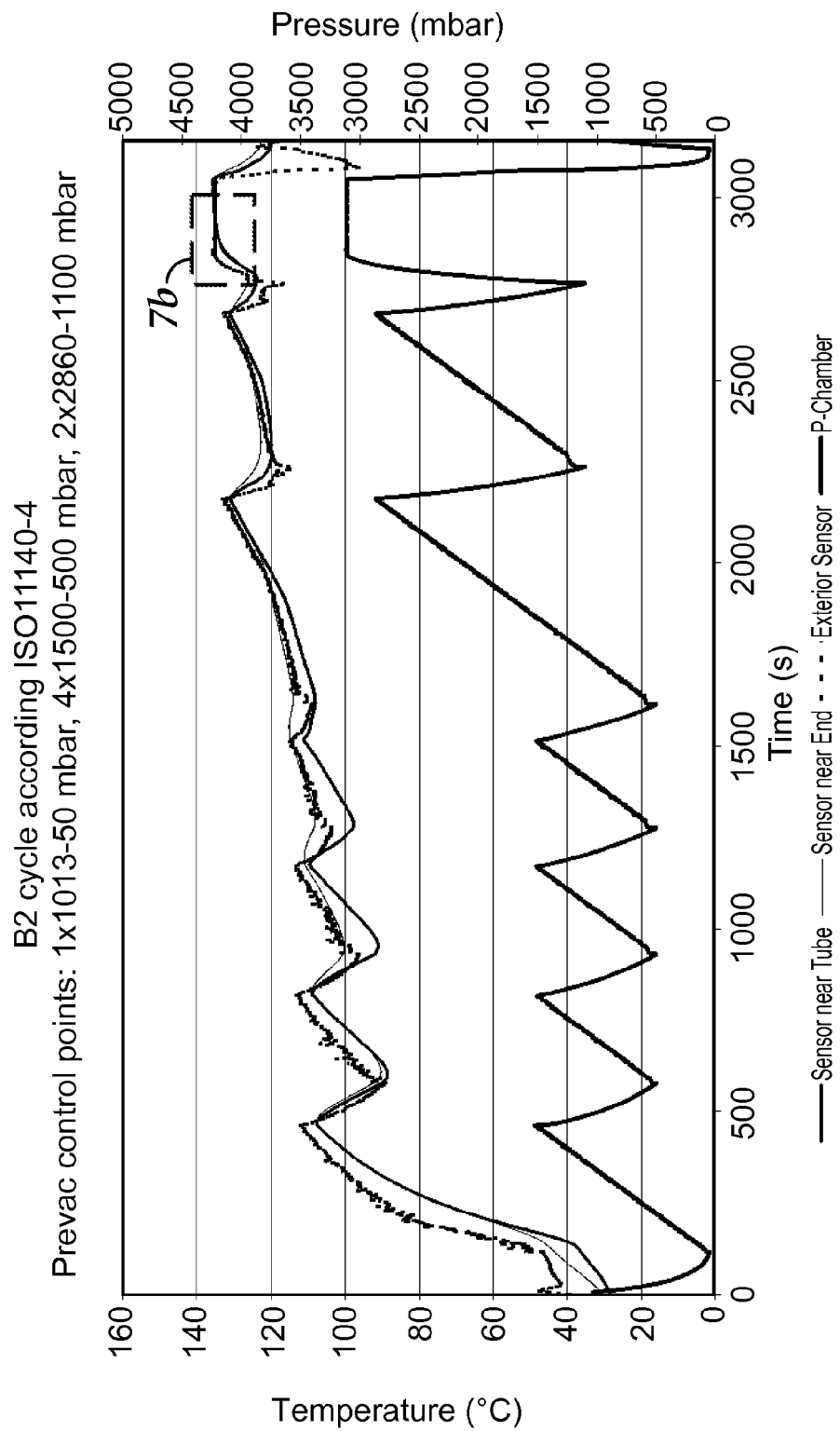
Figure 7B:
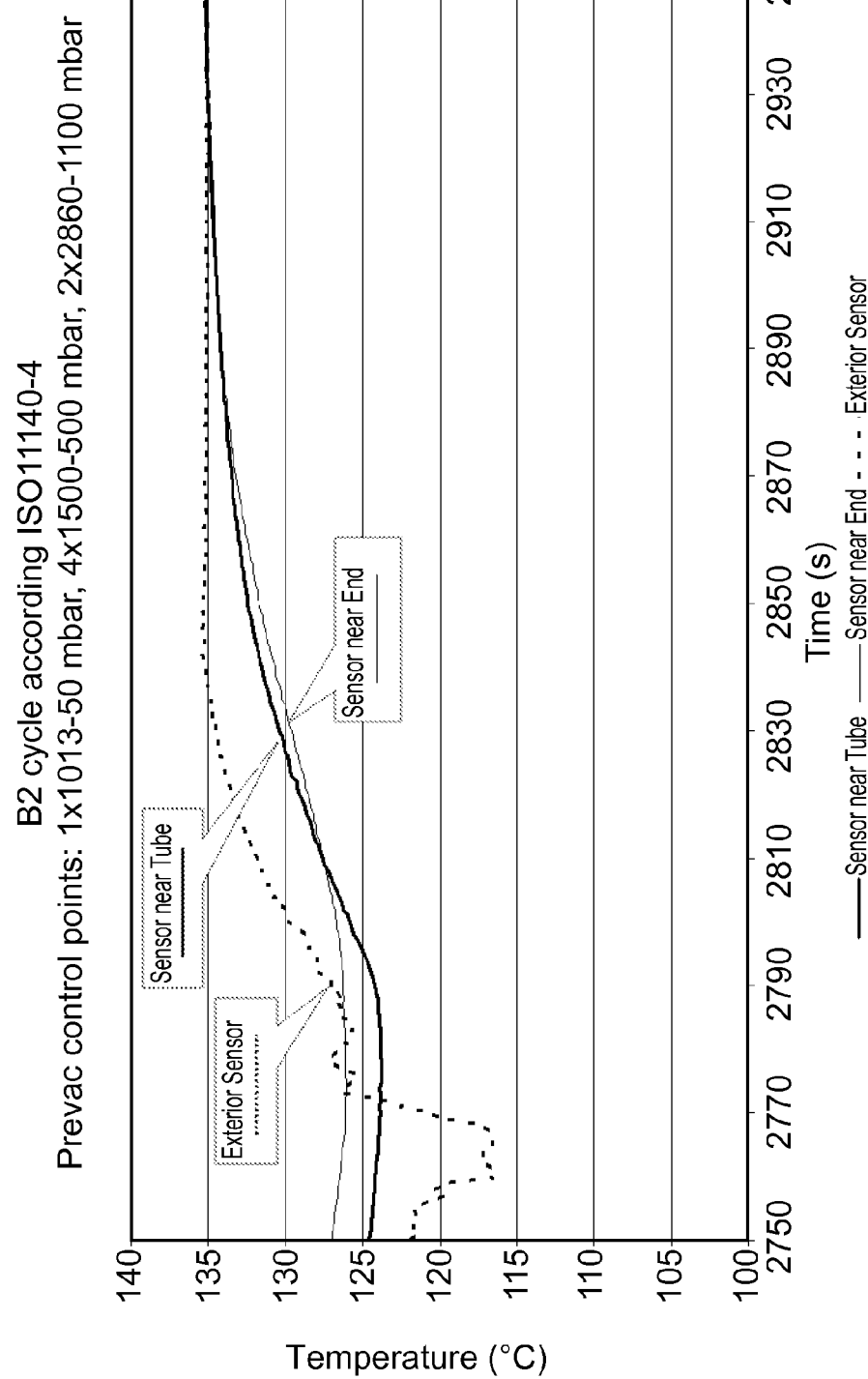
Figure 8A:
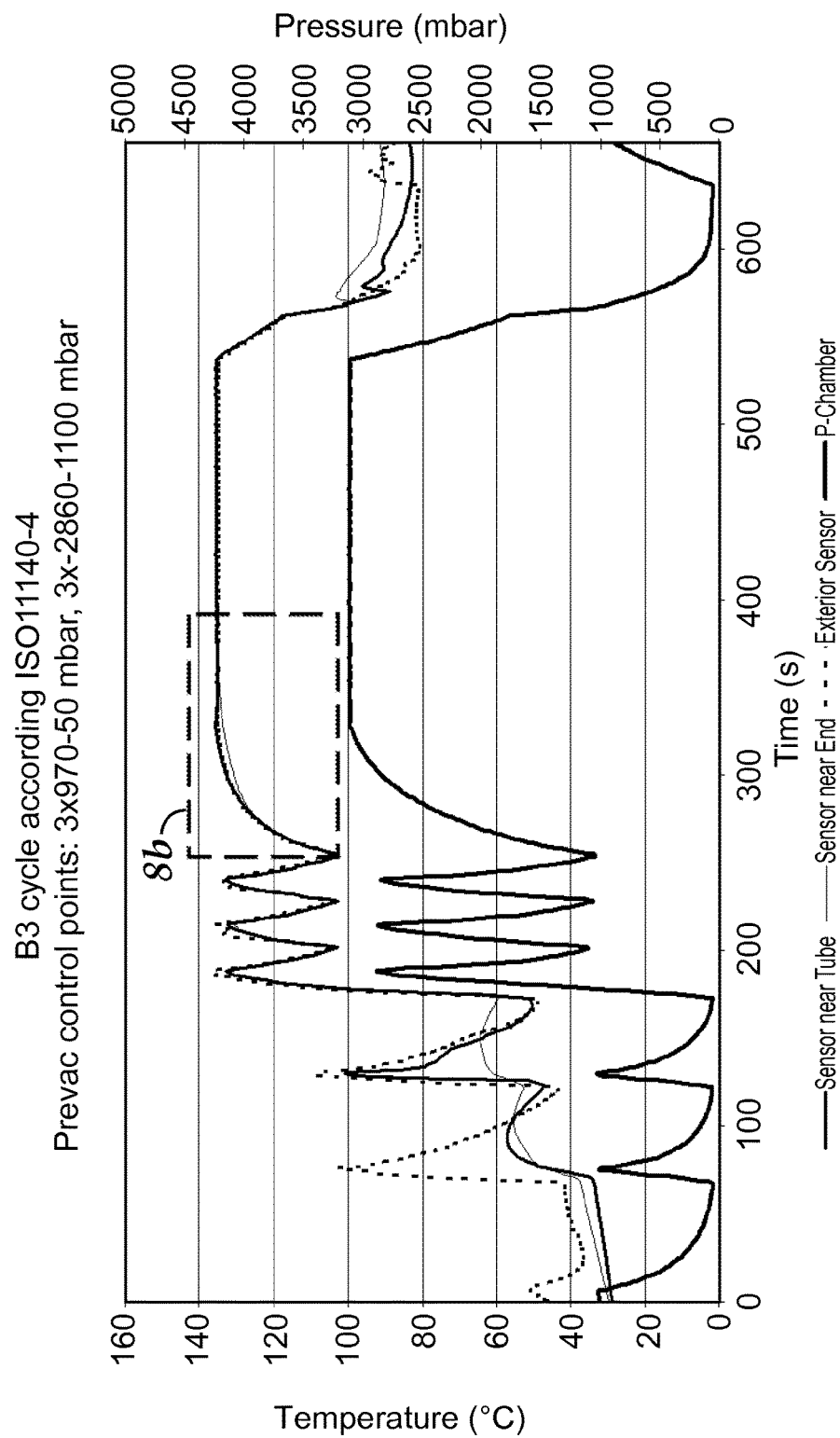
Figure 8B:
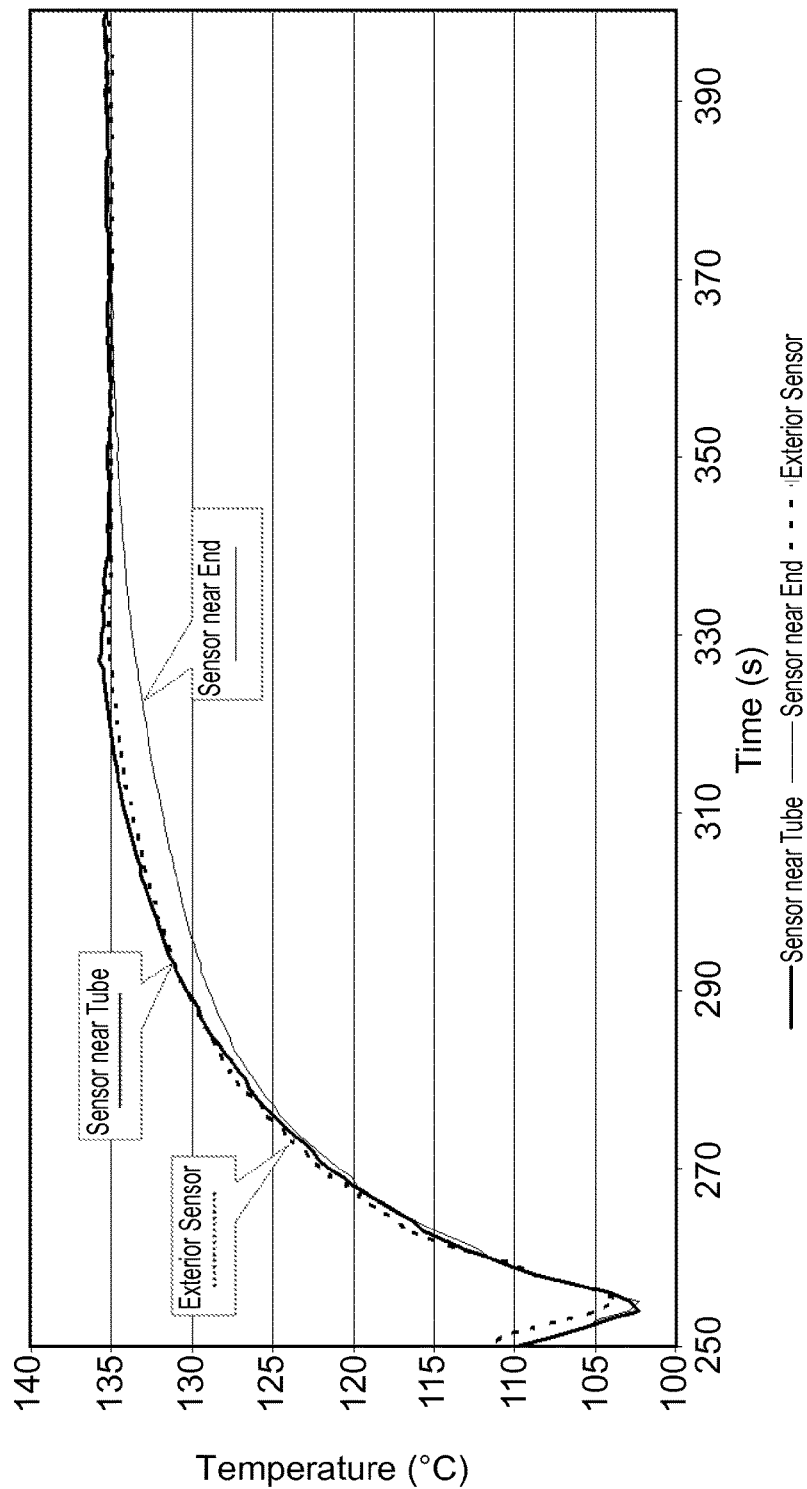

The observations gleaned from the experiments whose results are reported in FIGS. 7 and 8 suggest that the sterilization protocol used in these experiments, B2 and B3 of the ISO, may not lead to proper sterilization for hollow loads. In particular FIG. 7 shows the results of the monitoring of a standardized B2 pass cycle with the Example Device. As is evident from the encircled region in FIG. 7*a*, shown in detail in FIG. 7*b*, the temperature curves representing the measured temperatures at both thermocouples within the elongate tube show a largely reduced temperature rise in comparison to the measured external reference temperature curve (at the time it reaches 134° C.), while showing a small difference to each other. This suggests that there is a large air bubble present within the elongate tube along the length of the elongate tube (i.e. near its the closed end as well as near its open end that attached to the coiled tubing), even though B2 provided a "pass" for this test cycle. FIG. 8 shows the results of the monitoring of the standardized test cycle B3 with super-atmospheric pulsing. In this case, again at the point in time when the reference temperature reaches 134° C., temperature near the closed end of the elongate tube relative to both the other challenged temperature and the reference temperature shows a reduced temperature rise (see e.g. FIG. 8*b*). Accordingly, some air is still present within the elongate tube suggesting that this protocol would not provide proper sterilization for hollow loads.

As is evident from the above examples, devices in accordance to the present disclosure are extremely sensitive to sterilization conditions whereby the collected data may be processed and analyzed in various ways to provide information about cycle efficacy or any imperfections in the sterilization cycle.

An already indicated above, a difference greater than zero between challenged temperatures, e.g. challenged temperature far from closed end and challenged temperature near to closed end of elongate tube in the Example Device, is indicative of air in the elongate tube. The higher the temperature difference, the greater the amount of air there is. When the difference approaches zero then the slope air/steam gradient is becoming flat and the amount of steam is becoming equal at measured challenged position. Also a difference greater than zero between reference temperature and a challenged temperature is indicative of air in the elongate tube relative to the interior of the sterilization chamber. So for example at the point in time when the reference temperature reaches 134° C. and either one or all of the challenged temperatures are lagging behind (see e.g. FIG. 6), let's say at a value of 125° C., it can be concluded that air is present in the elongate tube.

The slopes of the measured curves may also be used to assess the particular sterilization cycle. In general, once the reference temperature reaches its sterilization temperature (e.g., 134° C.), the change in challenged temperatures should be equal to the change external to the device, for example in FIG. 3 curves 15, 16 and 17 should have the same slope. The larger the difference between these slopes the more air is present within the elongate tube.

In addition the efficiency of the pre-vacuum phase i.e. air removal is displayed in the slope of the temperature curves during the come-up phase Ideally the slope of challenged temperature curves (e.g. curves 15 and 16 in FIG. 3) should overlap the reference temperature curve (curve 17 in FIG. 3). If the exterior reference temperature sensor is exposed to steam, whereas the interior challenged temperature sensors are exposed to an air-steam mixture due to poor air removal during pre-vacuum phase, one or more of the interior challenged temperature curves will show a less steep incline as the exterior reference temperature (e.g. as mentioned in conjunction with a number of examples supra).

Figure 9:
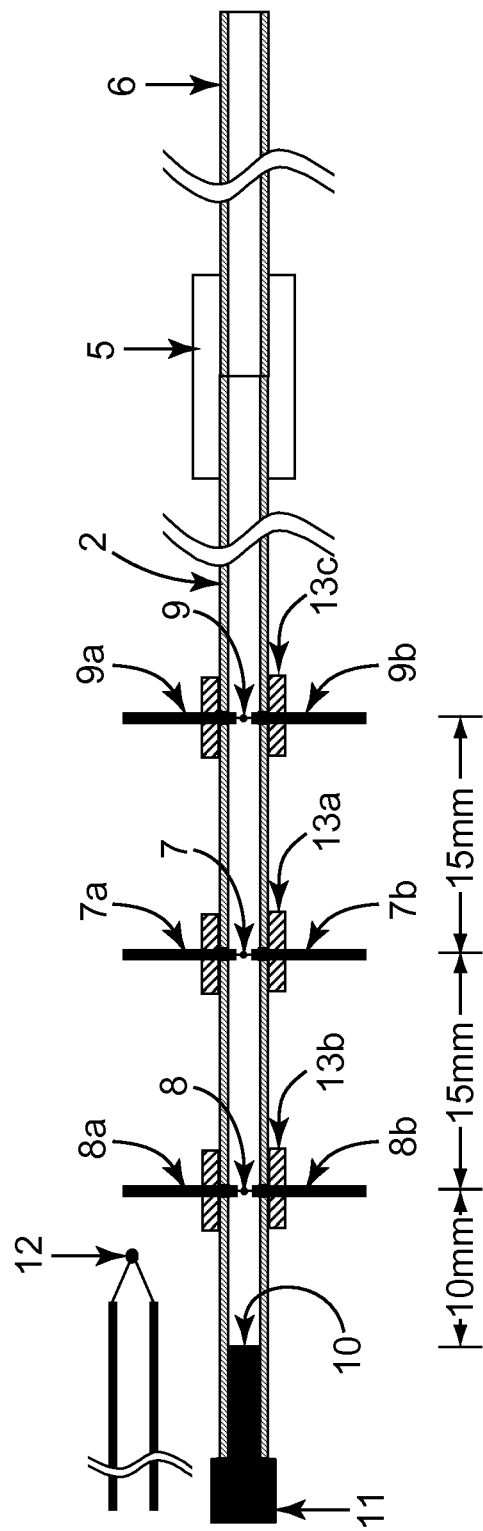
FIG. 9 shows a schematic and partial illustration of a further exemplary embodiment of a device for determining sterilization conditions within a sterilization chamber in accordance to the present disclosure.

FIG. 9 provides a schematic illustration of a further exemplary embodiment of a device in accordance to the present disclosure. As in the exemplary embodiment discussed supra one end of the elongate tube 2 is open while the other end is closed. Here the closed end is closed by a separate closing element, e.g., by means of an insulating plug 11. It can be advantageous to be able to open and close the closed end of the elongate tube between runs for example to allow the internal cavity to dry out easier. In this exemplary embodiment three temperature sensors, e.g. in the form of thermocouples 7, 8 and 9, are provided within the cavity of the elongate tube; the thermocouples being spaced apart from each other along the length of the elongate tube by a predetermined distance and spaced apart from the interior wall of the elongate tube. In the exemplary embodiment shown in FIG. 9, thermocouples are equally spaced apart from each other by 15 mm. This distance may however be altered between 5 mm and up to 40 mm as desired or needed. Similarly the spacings need not be equal, they may also vary so long they are predetermined. For example, the distance between thermocouples 7 and 9 may be twice as large as the distance between the thermocouples 7 and 8. As with the other illustrated exemplary embodiment it is desirable to have one temperature sensor, here thermocouple 8, positioned close to the closed end 10 of the elongate tube 2. In general, it is preferred that the thermocouples are arranged to be substantially thermally disconnected from the exterior of the elongate tube except through the opening at the open end of the elongate tube. The closed end 10 of the elongate tube is preferably closed with an insulating material such as polysiloxane. Similar to the exemplary embodiment described supra, the passages in the wall of the elongate tube through which the wires of the thermocouples extend are preferably sealed with a thermally insulating material such as a siloxane, in particular a polysiloxane, more particularly a vinyl polysiloxane. Preferably, the external opening of each passage together with each wire passing therethrough is covered with a collar 13*a* to *c*, preferably a collar made of a siloxane, such as a polysiloxane, in particular vinyl polysiloxane. Furthermore, the wires 7A, 7B, 8A, 8B, 9A and 9B forming the thermocouples are desirably sealed with a insulation jacket as suggested in FIG. 9. The elongate tube 2 is preferably configured to be coupled, more preferably releasably coupled, to an elongate lumen, e.g. a narrow tubing 6. The narrow tubing may having a length of between 1 m and 2 m, preferably of about 1.5 m, e.g., an coiled tubing similar to that shown in FIG. 1.

Advantageously, the elongate tube may be reused several times. If an elongate lumen is releaseably coupled onto the elongate tube, the de-coupled elongate lumen may be disposed as needed or desired. Favourably in use temperature transfer occur substantially only through of the passageway along the length of the elongate tube (or if a elongate lumen is coupled on to the elongate tube the passageway along the length of the elongate lumen and elongate tube) from the open end of elongate tube (or if applicable the open end of the elongate lumen) to the closed end of the elongate tube.

It will be understood that the disclosure is not limited to the exemplary embodiments and methods of use above-described and that various modifications can be made without departing from the principles or concepts of the disclosure described herein. For example, it will be appreciated that the design of the exemplary device-embodiments shown herein may be easily modified to allow the provision of four or more thermocouples.

Devices and methods in accordance to the disclosure may include appropriately any feature described herein separately or in combination with any other feature(s).

Embodiments

Embodiment 1 is a device for determining sterilization conditions within a sterilization chamber, said device comprising an elongate tube to be placed within said sterilization chamber, said tube having a tube wall and a cavity therein and being open at one end and closed at the other end thereof, and at least two temperature sensors within the cavity of the elongate tube, the at least two temperature sensors being spaced apart from each other along the length of the elongate tube by a predetermined distance and being spaced apart from the interior wall of the elongate tube.

Embodiment 2 is the device according to embodiment 1, wherein the at least two temperature sensors are arranged to be substantially thermally disconnected from the exterior of the elongate tube except through the opening at the open end of the elongate tube.

Embodiment 3 is the device according to embodiment 1 or 2, further comprising a processor adapted to determine, on the basis of the temperatures measured by the at least two temperature sensors within said tube in conjunction with a reference temperature determined at a location within the sterilization chamber but external to the elongate tube, whether predetermined sterilization conditions are met within said sterilization chamber.

Embodiment 4 is the device according to any of embodiments 1 to 3, wherein the device further comprises a temperature sensor external to the elongate tube and/or a pressure sensor external to the elongate tube.

Embodiment 5 is the device according to embodiment 3 or embodiment 4 as dependent on embodiment 3, wherein the reference temperature is either measured by said temperature sensor external to the tube or calculated on the basis of a pressure measured by said pressure sensor external to the tube.

Embodiment 6 is the device according to any of embodiments 1 to 5, wherein the at least two temperature sensors within the elongate tube each comprise a thermocouple, preferably a type T or type R or type S or type B thermocouple.

Embodiment 7 is the device according to embodiment 6, wherein the wall of the elongate tube comprises at least two passages therethrough, and each thermocouple comprises two wires, each wire extending through a passage in the tube wall.

Embodiment 8 is the device according to embodiment 7, wherein the elongate tube is cylindrical and wherein the wires extend radially through the tube and the thermocouple-forming ends are connected with each other at a location essentially on the central axis of the tube.

Embodiment 9 is the device according to embodiment 7 or 8, wherein the interior of each passage together with each wire passing therethrough is sealed with a sealing material, e.g. with a siloxane, in particular a polysiloxane, more particularly a vinyl polysiloxane.

Embodiment 10 is the device according to any of embodiments 7 to 9, wherein the external opening of each passage together with each wire passing therethrough is covered with a collar, preferably a collar made of a siloxane, more preferably a polysiloxane, most preferably a vinyl polysiloxane.

Embodiment 11 is the device according to any of embodiments 7 to 10, wherein each wire has a diameter of equal to or less than 0.4 mm, preferably equal to or less than 0.350 mm, more preferably equal to or less than 0.2 mm.

Embodiment 12 is the device according to any of the previous embodiments, wherein the device comprises three, four, five, six or more temperature sensors within the tube.

Embodiment 13 is the device according to any of the previous embodiments, wherein the temperature sensors are equally spaced from each other, Embodiment 14 is the device according to any of the previous embodiments, wherein the temperature sensors within the elongate tube are spaced from each other at a distance from 5 mm up to and including 40 mm, more preferably from 10 mm up to and including 30 mm.

Embodiment 15 is the device according to any of the previous embodiments, wherein at least one of said temperature sensors is located near the closed end of the elongate tube.

Embodiment 16 is the device according to any of the previous embodiments, wherein at least one of the temperature sensors is located at a distance from the interior wall of the closed end in the range 0.5 to 6 times the radius of inner diameter of elongate tube, in particular in the range 1 to 4 times the radius of inner diameter of elongate tube.

Embodiment 17 is the device according to any of the previous embodiments, wherein the elongate tube is configured so that it can be coupled to an elongate lumen, preferably the elongate tube is configured so that it can be releasably coupled to an elongate lumen.

Embodiment 18 is the device according to any of the previous embodiments, wherein the elongate tube is coupled to an elongate lumen, in particular the elongate tube is releasably coupled to an elongate lumen.

Embodiment 19 is the device according to embodiment 17 or 18, wherein the elongate lumen has a length of between 1 m and 2 m, preferably of about 1.5 m.

Embodiment 20 is the device according to any of embodiments 17 to 19, wherein the elongate lumen has an inner diameter of 10 mm or less, preferably 8 mm or less, more preferably 6 mm or less, or even more preferably 4 mm or less, and most preferably about 2 mm.

Embodiment 21 is the device according to any of embodiments 17 to 20, wherein the elongate lumen has along its length a wall thickness of 4 mm or less, more preferably 3 mm or less, even more preferably 2 mm or less, most preferably 2 mm down to and including 0.35 mm.

Embodiment 22 is the device according to any of the previous embodiments, wherein the elongate tube has an inner diameter of 10 mm or less, preferably 8 mm or less, more preferably 6 mm or less, or even more preferably 4 mm or less, and most preferably about 2 mm.

Embodiment 23 is the device according to any of the previous embodiments, wherein the elongate tube has along its length a wall thickness of 4 mm or less, more preferably 3 mm or less, even more preferably 2 mm or less, most preferably 2 mm down to and including 0.35 mm.

Embodiment 24 is a method for determining sterilization conditions within a sterilization chamber, preferably by using the device according to any of embodiments 1 to 16, the method comprising the following steps:

a) performing a predetermined sterilization protocol;
b) measuring, during said protocol, at least a first and a second temperature at first and second locations within an elongate tube situated within said sterilization chamber;
c) determining a reference temperature at a location within said sterilization chamber and external to the elongate tube during said protocol;
d) determining, on the basis of at least the first and second temperatures and the reference temperature, whether predetermined sterilization conditions are met within said sterilization chamber.

Embodiment 25 is the method according to embodiment 24, wherein the elongate tube is non-fixedly situated within the sterilization chamber.

Embodiment 26 is the method according to embodiment 24 or 25, wherein the elongate tube is placed into the sterilization chamber prior to start of the protocol.

Embodiment 27 is the method according to any of embodiments 24 to 26, wherein said reference temperature is determined either by measuring, during the protocol, a temperature at a location within said sterilization chamber and external to the elongate tube or by calculating said reference temperature on the basis of a pressure measured during the protocol at a location within said sterilization chamber and external to the elongate tube.

Embodiment 28 is the method according to any of embodiments 24 or 27, further comprising measuring, during said protocol, at least one further temperature at at least one further location within said elongate tube.

Embodiment 29 is the method according to any of embodiments 24 to 28, wherein step d) is performed on the basis of the difference between the first and second temperatures and, if applicable, said further temperatures and/or on the basis of the temperature gradient within said elongate tube at a point of time during the protocol.

Embodiment 30 is the method according to any of embodiments 24 to 29, wherein step d) is performed on the basis of the increase of the first and/or second and/or, if applicable, said further temperatures during a time interval during the protocol.

Embodiment 31 is the method according to any of embodiments 24 to 30, wherein said elongate tube is open at one end and closed at the other end thereof.

Embodiment 32 is the method according to embodiment 31, and wherein said first, second and, if applicable, further locations within the elongate tube are substantially thermally disconnected from the exterior of the elongate tube except through the opening at the open end of the elongate tube.

Embodiment 33 is the method according to embodiment 31 or 32, wherein at least one of said locations within the elongate tube is located near the closed end of the elongate tube.

Embodiment 34 is the method according to any of embodiments 31 to 33, wherein at least one of the locations within the elongate tube is located at a distance from the interior wall of the closed end in the range 0.5 to 6 times the radius of inner diameter of elongate tube, in particular in the range 1 to 4 times the radius of inner diameter of elongate tube.

Embodiment 35 is the method according to any of embodiments 24 to 34, wherein the locations within the elongate tube are spaced from each other at a distance from 5 mm up to and including 40 mm, more preferably from 10 mm up to and including 30 mm.

What is claimed is:

1. A device for determining sterilization conditions within a sterilization chamber, said device comprising an elongate tube to be placed within said sterilization chamber, said tube having a tube wall and a cavity therein and being open at one end and closed at the other end thereof, and at least two temperature sensors within the cavity of the elongate tube, wherein the at least two temperature sensors within the elongate tube each comprise a thermocouple and the at least two temperature sensors being spaced apart from each other along the length of the elongate tube by a predetermined distance and being spaced apart from an interior wall of the elongate tube;

wherein the wall of the elongate tube comprises at least first and second passages therethrough adjacent to each thermocouple, and each thermocouple comprises two wires, one wire extending through the first passage and the other wire extending through the second passage in the tube wall, wherein each wire has a thermocouple forming end for each thermocouple, the thermocouple forming ends of the two wires are connected, wherein each wire has a diameter of equal to or less than 0.4 mm wherein the device further comprises a processor adapted to determine, on the basis of the temperatures measured by the at least two temperature sensors within said tube in conjunction with a reference temperature determined at a location within the sterilization chamber but external to the elongate tube, whether predetermined sterilization conditions are met within said sterilization chamber, and wherein the device further comprises a pressure sensor external to the elongate tube.

2. The device according to claim 1, wherein the at least two temperature sensors are arranged to be substantially thermally disconnected from the exterior of the elongate tube except through the opening at the open end of the elongate tube.

3. The device according to claim 1, wherein the reference temperature is measured by said temperature sensor external to the elongate tube.

4. The device according to claim 1, wherein the reference temperature is calculated on the basis of a pressure measured by said pressure sensor external to the elongate tube.

5. The device according to claim 1, wherein the elongate tube is cylindrical and wherein the wires extend radially through the tube and the thermocouple forming ends are connected with each other at a location essentially on the central axis of the tube.

6. The device according to claim 1, wherein the device comprises three or more temperature sensors within the tube.

7. The device according to claim 6, wherein the temperature sensors within the elongate tube are spaced from each other at a distance from 5 mm up to and including 40 mm.

8. The device according to claim 6, wherein at least one of the temperature sensors is located at a distance from the interior wall of the closed end in the range 0.5 to 6 times the radius of inner diameter of elongate tube.

9. The device according to claim 1, wherein the elongate tube is configured so that it can be coupled to an elongate lumen.

10. The device according to claim 9, wherein the elongate tube is releasably coupled to the elongate lumen.

11. The device according to claim 9, wherein the elongate lumen has a length of between 1 meter and 2 meters; an inner diameter of 10 mm or less; and has along its length a wall thickness of 4 mm or less.

12. A method for determining sterilization conditions within a sterilization chamber, using the device according to claim 1, the method comprising the following steps:
a) performing a predetermined sterilization protocol;
b) measuring, during said protocol, at least a first and a second temperature at first and second locations within the elongate tube situated within said sterilization chamber;
c) determining a reference temperature at a location within said sterilization chamber and external to the elongate tube during said protocol;
d) determining, on the basis of at least the first and second temperatures and the reference temperature, whether predetermined sterilization conditions are met within said sterilization chamber.

* * * * *